(12) United States Patent
Treu et al.

(10) Patent No.: US 8,853,420 B2
(45) Date of Patent: Oct. 7, 2014

(54) COMPOUNDS

(75) Inventors: Matthias Treu, Vienna (AT); Thomas Karner, Vienna (AT); Ulrich Reiser, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 210 days.

(21) Appl. No.: 13/125,841

(22) PCT Filed: Jul. 28, 2009

(86) PCT No.: PCT/EP2009/059770
§ 371 (c)(1),
(2), (4) Date: May 16, 2011

(87) PCT Pub. No.: WO2010/012747
PCT Pub. Date: Feb. 4, 2010

(65) Prior Publication Data
US 2011/0263565 A1 Oct. 27, 2011

(30) Foreign Application Priority Data
Jul. 29, 2008 (EP) ..................................... 08161381

(51) Int. Cl.
| | | |
|---|---|---|
| C07D 209/34 | (2006.01) | |
| C07D 401/10 | (2006.01) | |
| C07D 403/10 | (2006.01) | |
| C07D 403/14 | (2006.01) | |
| C07D 413/14 | (2006.01) | |
| C07D 405/10 | (2006.01) | |
| C07D 405/12 | (2006.01) | |
| C07D 403/12 | (2006.01) | |
| C07D 405/06 | (2006.01) | |
| C07D 405/04 | (2006.01) | |
| C07D 401/06 | (2006.01) | |
| C07D 403/04 | (2006.01) | |
| C07D 487/10 | (2006.01) | |
| C07D 405/14 | (2006.01) | |
| C07D 401/14 | (2006.01) | |
| C07D 401/04 | (2006.01) | |
| C07D 471/08 | (2006.01) | |

(52) U.S. Cl.
CPC ............ *C07D 209/34* (2013.01); *C07D 401/10* (2013.01); *C07D 405/10* (2013.01); *C07D 405/12* (2013.01); *C07D 403/12* (2013.01); *C07D 413/14* (2013.01); *C07D 405/06* (2013.01); *C07D 405/04* (2013.01); *C07D 401/06* (2013.01); *C07D 403/04* (2013.01); *C07D 487/10* (2013.01); *C07D 405/14* (2013.01); *C07D 401/14* (2013.01); *C07D 401/04* (2013.01); *C07D 403/10* (2013.01); *C07D 403/14* (2013.01); *C07D 471/08* (2013.01)
USPC ........................................................ 548/486

(58) Field of Classification Search
CPC .. C07D 209/34; C07D 401/10; C07D 403/10; C07D 403/14; C07D 413/14; C07D 405/10
USPC .......................................................... 548/486
See application file for complete search history.

(56) References Cited

U.S. PATENT DOCUMENTS

| | | | |
|---|---|---|---|
| 6,762,180 | B1 | 7/2004 | Roth et al. |
| 6,794,395 | B1 | 9/2004 | Roth et al. |
| 6,855,710 | B2 | 2/2005 | Walter et al. |
| 6,858,641 | B2 | 2/2005 | Roth et al. |
| 7,148,249 | B2 | 12/2006 | Kley et al. |
| 7,169,936 | B2 | 1/2007 | Roth et al. |

FOREIGN PATENT DOCUMENTS

| | | |
|---|---|---|
| CA | 2381821 A1 | 8/2001 |
| WO | 0018734 A1 | 4/2000 |
| WO | 0073297 A1 | 12/2000 |
| WO | 0116130 A1 | 3/2001 |
| WO | 0127081 A1 | 4/2001 |
| WO | 02081445 A1 | 10/2002 |
| WO | 2004009547 A1 | 1/2004 |
| WO | 2004026829 A2 | 4/2004 |
| WO | 2004096224 A2 | 11/2004 |
| WO | 2006067165 A2 | 6/2006 |
| WO | 2006067168 A1 | 6/2006 |
| WO | 2007057397 A1 | 5/2007 |
| WO | 2007122219 A1 | 11/2007 |
| WO | 2007141283 A2 | 12/2007 |

(Continued)

OTHER PUBLICATIONS

Cancer and Metastasis Reviews (1998), 17(1), 91-106.*

(Continued)

*Primary Examiner* — Shawquia Young
(74) *Attorney, Agent, or Firm* — Michael P. Morris; Mary-Ellen M. Devlin

(57) ABSTRACT

The present invention encompasses compounds of general formula (1), wherein $R^1$ to $R^4$ are defined as in claim 1, which are suitable for the treatment of diseases characterized by excessive or abnormal cell proliferation, and their use for preparing a medicament having the above-mentioned properties.

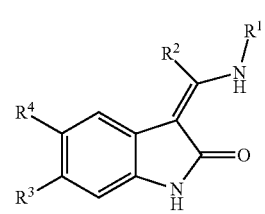

(1)

15 Claims, No Drawings

(56) References Cited

FOREIGN PATENT DOCUMENTS

| WO | 2010007114 A2 | 1/2010 |
|---|---|---|
| WO | 2010007116 A2 | 1/2010 |
| WO | 2010012740 A1 | 2/2010 |
| WO | 2010014586 A1 | 2/2010 |

OTHER PUBLICATIONS

Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Roth, et al. Document No. 134:222621 retrieved from CAPLUS; Mar. 8, 2001.*
Database Caplus (online) Chemical Abstracts Service, Columbus, OH; Nov. 18, 2008; Database Accession No. 2001:167990 abstract.
International Search Report, Form PCT/ISA/210, for corresponding PCT/EP2009/059770; date of mailing: Sep. 22, 2009.
Abstract: ChemSPider (ChemZoo, Inc.); STN on the Web, file registry, RN=1027399-56-9, 1027062-57-2, 1025924-35-9,674771-67-6, 334991-98-9, 334950-21-9, 334950-19-5, 334950-17-3, 334950-15-1, 334950-13-9, 334950-11-7, 334950-09-3, 334950-07-1, 334949-79-0, 334949-71-2, 334949-66-5, 334949-63-2, 334949-61-0, 334949-57-4, 334949-55-2, 334949-53-0, 334949-51-8, 334949-49-4, 334949-47-2, 334949-45-0, 334949-43-8, 334949-41-6, Jun. 2008, 13 pages.

* cited by examiner

COMPOUNDS

The present invention relates to new indolinones of general formula (1),

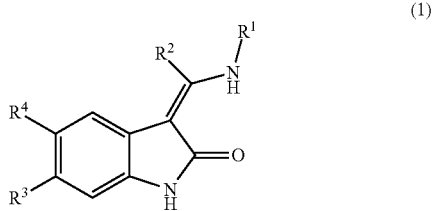

wherein the groups $R^1$ to $R^4$ have the meanings given in the claims and specification, the isomers thereof, processes for preparing these indolinones and their use as medicaments.

The aim of the present invention is to indicate new active substances which may be used for the prevention and/or treatment of diseases characterised by excessive or abnormal cell proliferation.

BACKGROUND TO THE INVENTION

Indolinones are described for example as receptor tyrosinekinases and cyclin/CDK-complex inhibiting compounds, and are substituted in the 6 position either with a methyl carboxylate (WO02/081445), carbamoyl (WO01/27081) or with halogens (WO2004/026829).

DETAILED DESCRIPTION OF THE INVENTION

It has now been found that, surprisingly, compounds of general formula (1), wherein the groups $R^1$ to $R^4$ have the meanings given hereinafter act as inhibitors of specific cell cycle kinases. Thus, the compounds according to the invention may be used for example for the treatment of diseases connected with the activity of specific cell cycle kinases and characterised by excessive or abnormal cell proliferation.

The present invention relates to compounds of general formula (1),

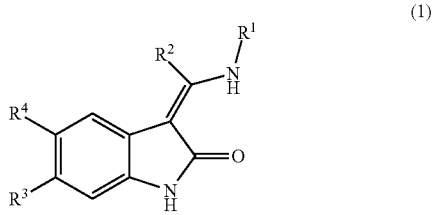

wherein $R^1$ denotes hydrogen or a group, optionally substituted by one or more identical or different $R^5$, selected from among $C_{3-10}$cycloalkyl, 3-8 membered heterocycloalkyl, $C_{6-15}$aryl and 5-15 membered heteroaryl; and $R^2$ denotes a group, optionally substituted by one or more identical or different $R^5$, selected from among $C_{6-15}$aryl and 5-15 membered heteroaryl; and $R^3$ denotes a group, optionally substituted by one or more identical or different $R^5$, selected from among $C_{1-6}$alkyl, $C_{2-6}$alkenyl, $C_{2-6}$alkynyl, $C_{6-15}$aryl and 5-12 membered heteroaryl, and $R^4$ is hydrogen, $C_{1-6}$alkyl or $R^b$, and $R^5$ each independently of one another denote a group selected from among $R^a$, $R^b$ and $R^a$ substituted by one or more identical or different $R^b$ and/or $R^c$; and each $R^a$ is selected independently from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^b$ is a suitable group and each is independently selected from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$ and —$N(R^g)C(NR^g)NR^cR^c$, each $R^c$ independently of one another denotes hydrogen or a group optionally substituted by one or more identical or different $R^d$ and/or $R^e$ selected from among $C_{1-6}$alkyl, $C_{2-6}$alkenyl, $C_{2-6}$alkynyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^d$ is a suitable group and each is independently selected from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —CN, —NC, —OCN, —SCN, —NO, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$, —$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$ and —$N(R^g)C(NR^g)NR^eR^e$, each $R^e$ independently of one another denotes hydrogen or a group optionally substituted by one or more identical or different $R^f$ and/or $R^g$ selected from among $C_{1-6}$alkyl, $C_{2-6}$alkenyl, $C_{2-6}$alkynyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^f$ is a suitable group and each is independently selected from among halogen, —$CF_3$ and —$NR^gR^g$; and each $R^g$ independently of one another denotes hydrogen, $C_{1-6}$alkyl, $C_{2-6}$alkenyl, $C_{2-6}$alkynyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl, optionally in the form of the prodrugs, the tautomers, the racemates, the enantiomers, the diastereomers and the mixtures thereof, and optionally the pharmacologically acceptable acid addition salts thereof, with the proviso that in the event that $R^3$ is phenyl, this is at least substituted by an $R^b$, and with the proviso that 3-(Z)-{1-[4-(piperidin-1-yl-methyl)-anilino]-1-phenyl-methylidene}-6-(pyrrol-1-yl)-2-indolinone and 3-(Z)-{1-[4-(piperidin-1-yl-methyl)-anilino]-1-phenyl-methylidene}-6-(pyrrolidin-1-yl)-2-indolinone are excluded.

In one aspect the invention relates to compounds of general formula (1), wherein $R^3$ is $C_{6-15}$aryl or 5-12 membered heteroaryl.

In another aspect the invention relates to compounds of general formula (1), wherein $R^3$ is phenyl.

In another aspect the invention relates to compounds of general formula (1), wherein $R^3$ is selected from among furan, pyrazole, pyridine, pyrimidine and pyrazine.

In another aspect the invention relates to compounds of general formula (1), wherein $R^4$ is hydrogen.

In another aspect the invention relates to compounds of general formula (1), wherein $R^3$ is $C_{1-6}$alkyl, $C_{2-6}$alkenyl or $C_{2-6}$alkynyl.

In another aspect the invention relates to compounds of general formula (1), wherein $R^3$ is $C_{2-6}$alkynyl.

In another aspect the invention relates to compounds of general formula (1), wherein $R^2$ is phenyl.

In another aspect the invention relates to compounds of general formula (1), wherein $R^2$ denotes unsubstituted phenyl.

In another aspect the invention relates to compounds of general formula (1), or the pharmaceutically effective salts thereof, as medicaments.

In another aspect the invention relates to compounds of general formula (1), or the pharmaceutically effective salts thereof, for preparing a medicament with an antiproliferative activity.

In another aspect the invention relates to a pharmaceutical preparation, containing as active substance one or more compounds of general formula (1) or the physiologically acceptable salts thereof, optionally in combination with conventional excipients and/or carriers.

In another aspect the invention relates to the use of compounds of general formula (1) for preparing a medicament for the treatment and/or prevention of cancer, infections, inflammations and autoimmune diseases.

In another aspect the invention relates to a pharmaceutical preparation comprising a compound of general formula (1) and at least one further cytostatic or cytotoxic active substance, different from formula (1), optionally in the form of the tautomers, the racemates, the enantiomers, the diastereomers and the mixtures thereof, and optionally the pharmacologically acceptable acid addition salts thereof.

DEFINITIONS

As used herein, the following definitions apply, unless stated otherwise.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms.

Examples of individual sub-groups are listed below.

Straight-Chain (Unbranched) or Branched, Saturated Hydrocarbon Chains:

methyl; ethyl; n-propyl; isopropyl (1-methylethyl); n-butyl; 1-methylpropyl; isobutyl (2-methylpropyl); sec.-butyl (1-methylpropyl); tert.-butyl (1.1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chained (Unbranched) or Branched Alkenyl:

vinyl (ethenyl); prop-1-enyl; allyl (prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. unless otherwise stated are meant unsaturated hydrocarbon groups with the corresponding number of carbon atoms and a triple bond, including all the isomeric forms.

By the term heteroalkyl are meant groups which are derived from the alkyl as hereinbefore defined in its widest sense by replacing, in the hydrocarbon chains, one or more of the groups —CH₃ independently of one another by the groups —OH, —SH or —NH₂, one or more of the groups —CH₂— independently of one another by the groups —O—, —S— or —NH—, one or more of the groups

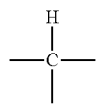

by the group

one or more of the groups =CH— by the group =N—, one or more of the groups =CH₂ by the group =NH or one or more of the groups =CH by the group =N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom.

The following are listed by way of example:
dimethylaminomethyl; dimethylaminoethyl (1-dimethylaminoethyl; 2-dimethylamino-ethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-diisopropylaminoethyl); bis-2-methoxyethylamino; [2-(dimethylamino-ethyl)-ethylamino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Halogen encompasses fluorine, chlorine, bromine and/or iodine atoms.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydrohalogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms.

Typical examples include, for example:
—CF₃; —CHF₂; —CH₂F; —CF₂CF₃; —CHFCF₃; —CH₂CF₃; —CF₂CH₃; —CHFCH₃; —CF₂CF₂CF₃; —CF₂CH₂CH₃; —CF=CF₂; —CCl=CH₂; —CBr=CH₂; —CI=CH₂; —C≡C—CF₃; —CHFCH₂CH₃; and —CHFCH₂CF₃.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono- or polysubstituted independently of one another at all the hydrogen-carrying carbon atoms. Cycloalkyl itself as a substituent may be attached to the molecule through any suitable position of the ring system.

The following individual sub-groups are listed by way of example:
Monocyclic Saturated Hydrocarbon Rings:
cyclopropyl; cyclobutyl; cyclopentyl; cyclohexyl; cycloheptyl etc.
Monocyclic Unsaturated Hydrocarbon Rings:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.
Saturated and Unsaturated Bicyclic Hydrocarbon Rings:
bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl (decahydronaphthalene); bicyclo[2.2.1]heptyl (norbornyl); (bicyclo[2.2.1]hepta-2,5-dienyl (norborna-2,5-dienyl); bicyclo[2.2.1]hept-2-enyl (norbornenyl); bicyclo[4.1.0]heptyl (norcaranyl); bicyclo-[3.1.1]heptyl (pinanyl) etc.
Saturated and Unsaturated Spirohydrocarbon Rings:
spiro[2.5]octyl, spiro[3.3]heptyl, spiro[4.5]dec-2-ene, etc.

Cycloalkylalkyl denotes the combination of the alkyl and cycloalkyl groups defined hereinbefore, in each case in their broadest sense. The alkyl group as substituent is directly linked to the molecule and is in turn substituted by a cycloalkyl group. The linking of alkyl and cycloalkyl in both groups may be effected by means of any suitable carbon atoms. The sub-groups of alkyl and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system.

Typical examples include phenyl, naphthyl, indanyl (2,3-dihydroindenyl), 1,2,3,4-tetrahydronaphthyl and fluorenyl.

Arylalkyl denotes the combination of the groups alkyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. The respective sub-groups of alkyl and aryl are also included in the combination of the two groups.

Typical examples include benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below.

Monocyclic Heteroaryls:

furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.

Polycyclic Heteroaryls:

indolyl; isoindolyl; benzofuryl; benzothienyl; benzoxazolyl; benzothiazolyl; benzisoxazolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydrothienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; cumarinyl; isocumarinyl; chromonyl; chromanonyl; tetrahydroquinolinyl; dihydroquinolinyl; dihydroquinolinonyl; dihydroisoquinolinonyl; dihydrocumarinyl; dihydroisocumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzo-thiopyranyl-S-oxide and benzothiopyranyl-S,S-dioxide etc.

Heteroarylalkyl denotes the combination of the alkyl and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose. The respective sub-groups of alkyl and heteroaryl are also included in the combination of the two groups.

By the term heterocycloalkyl are meant groups which are derived from the cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated):

tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-S-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydropyrimidinyl; dihydrofuryl; dihydropyranyl; tetrahydrothienyl-5-oxide; tetrahydrothienyl-S,S-dioxide; homothiomorpholinyl-S-oxide; 2,3-dihydroazet; 2H-pyrrolyl; 4H-pyranyl; 1,4-dihydropyridinyl etc.

Bicyclic Heterorings (Saturated and Unsaturated):

8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2]nonyl; hexahydro-furo[3,2-b]furyl; etc.

Spiro-Heterorings (Saturated and Unsaturated):

1,4-dioxa-spiro[4.5]decyl; 1-oxa-3.8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

Heterocycloalkylalkyl denotes the combination of the alkyl and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose. The respective sub-groups of alkyl and heterocycloalkyl are also included in the combination of the two groups.

By the term "suitable substituent" is meant a substituent which on the one hand is suitable by virtue of its valency and on the other hand leads to a system which is chemically stable.

By "prodrug" is meant an active substance in the form of its precursor metabolite. B distinction may be made between partly multi-part carrier-prodrug systems and biotransformation systems. The latter contain the active active substance in a form that requires chemical or biological metabolisation. The skilled man will be familiar with prodrug systems of this kind (Sloan, Kenneth B.; Wasdo, Scott C. The role of prodrugs in penetration enhancement. Percutaneous Penetration Enhancers (2nd Edition) (2006). 51-64; Lloyd, Andrew W. Prodrugs. Smith and Williams' Introduction to the Principles of Drug Design and Action (4th Edition) (2006), 211-232; Neervannan, Seshadri. Strategies to impact solubility and dissolution rate during drug lead optimization: salt selection and prodrug design approaches. American Pharmaceutical Review (2004), 7(5), 108.110-113). A suitable prodrug contains for example a substance of the general formulae which is linked via an enzymatically cleavable linker (e.g. carbamate, phosphate, N-glycoside or a disulphide group to a dissolution-improving substance (e.g. tetraethyleneglycol, saccharide, amino acids). Carrier-prodrug systems contain the active substance as such, bound to a masking group which can be cleaved by the simplest possible controllable mechanism. The function of masking groups according to the invention in the compounds according to the invention is to neutralise the charge for improving cell uptake. If the compounds according to the invention are used with a masking group, these may also additionally influence other pharmacological parameters, such as for example oral bioavailability, tissue distribution, pharmacokinetics and stability against non-specific phosphatases. The delayed release of the active substance may also involve a sustained-release effect. In addition, modified metabolisation may occur, thus resulting in a higher efficiency of the active substance or organic specificity. In the case of a prodrug formulation, the masking group or a linker that binds the masking group to the active substance is selected such that the prodrug is sufficienyl hydrophilic to be dissolved in the blood serum, has sufficient chemical and enzymatic stability to reach the activity site and is also sufficiently hydrophilic to ensure that it is suitable for diffusion-controlled membrane transport. Furthermore, it should allow chemically or ensymatically induced release of the active substance within a reasonable period and, it goes without saying, the auxiliary components released should be non-toxic. Within the scope of the invention, however, the compound without a mask or linker, and a mask, may be regarded as a prodrug which first of all has to be prepared in the cell from the ingested compound by enzymatic and biochemical processes.

1. Preparation of the Intermediates and Components
1.1. Indolinone Intermediates

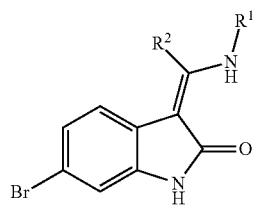

All the indolinone intermediate compounds that are not explicitly described are prepared using components obtained commercially or known from the literature using standard methods of synthesis or analogously to the methods described in WO 2007/122219 and PCT/EP2008057149 starting from 6-bromoindo linone, the preparation of which is described in WO2004009547.

1.2. Other Intermediate Compounds

1.2.1. 5-fluoro-6-bromo-indolinone

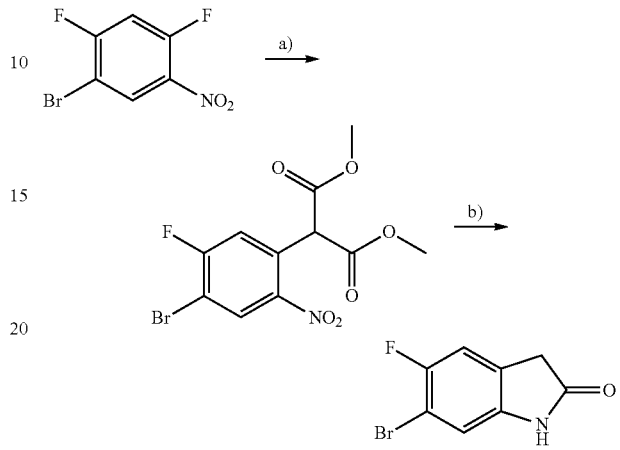

a) 1-Bromo-2,4-difluoro-5-nitrobenzene (2 g) is combined with 30 mL dioxane and 1.1 mL dimethylmalonate. While cooling by means of an ice bath, 0.8 g of a 60% sodium hydride suspension in mineral oil is added batchwise. Then the mixture is stirred at RT until the reaction is complete. The reaction mixture is combined with 5 mL saturated $NH_4Cl$ solution and extracted repeatedly with DCM. The combined organic phases are dried, filtered and freed from the volatile constituents in vacuo. The crude product is further used directly.

b) The crude product obtained is combined with 700 mg LiCl, 150 µL water and 50 mL DMSO and stirred for 3 h at 100° C. Then the reaction mixture is cooled to RT, combined with saturated saline solution and extracted repeatedly with EtOAc. The combined organic phases are dried, filtered and freed from the volatile constituents in vacuo. 20 mL acetic acid and 2 g iron powder are added to the remaining mixture which is then heated to 100° C. until 5-fluoro-6-bromo-indolinone has formed. The reaction mixture is freed from the volatile constituents, combined with EtOAc, filtered and the product is isolated by normal phase chromatography.

1.2.2. 5-$SO_2$-substituted indolinones

General Method for 5-amino-sulphonyl Compounds

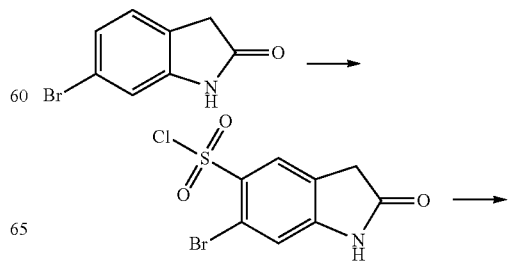

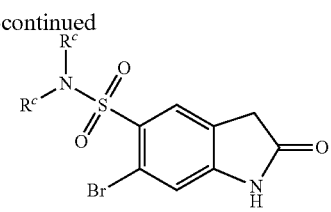

Chlorosulphonic acid (30 mL) is taken, cooled to 0° C. cooled and combined with 8 g of 6-bromoindolinone with vigorous stirring. The ice bath is removed and the mixture is stirred for a further 16 h at RT. The reaction mixture is slowly poured onto ice with vigorous stirring, the precipitate formed is filtered off and dried in the vacuum dryer. 6-Bromindolinone-5-sulphonyl chloride is obtained as crude product, which is further used directly.

The corresponding amine (1.62 mmol) is placed in 2 mL ACN together with 2 eq. iPr$_2$NEt. A mixture of 500 mg of 6-bromindolinone-5-sulphonyl chloride and 2 mL ACN is slowly added thereto with stirring. Once the reaction has ended the reaction mixture is extracted with water and several times with DCM. The combined organic phases are dried and freed from the volatile constituents in vacuo. The crude product obtained may be further used directly.

a) 6-bromo-5-(4-fluorophenylsulphonyl)-indolinone

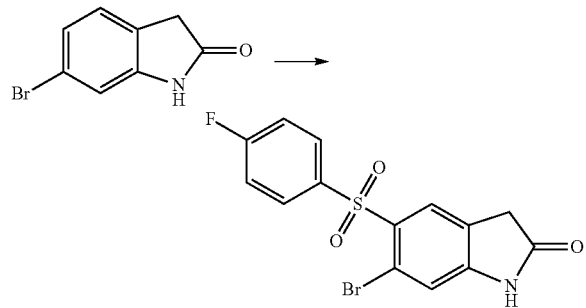

4-fluoro-benzolsulphonyl chloride (3.76 g) and aluminium chloride (10 g) are mixed with 40 mL of 1,2-dichloroethane and stirred for 1 h at RT. Then 4 g 6-bromoindolinone are added and the mixture is stirred for 5 h at 55° C. The reaction mixture is combined with water and EtOAc. The organic phase is separated off and the product is obtained by RP chromatography.

1.2.3. (5-Bromopyridin-2-yl)alkylamines

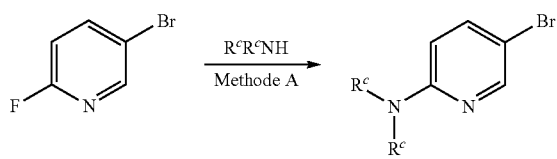

Method A) 5-Bromopyridin-2-yl)methylamines 2-fluoro-5-bromopyridine (2.00 g, 11.37 mmol), methylamine-hydrochloride (1.92 g, 28.40 mmol) and N-ethyldiisopropylamine (2.14 mL, 12.50 mmol) in NMP (10 mL) are stirred for 40 min in a microwave reactor at 140° C. The crude mixture is purified by normal phase chromatography. Yield: 1.33 g (63%).

1.2.4. (5-Bromopyrimidin-2-yl)alkylamines

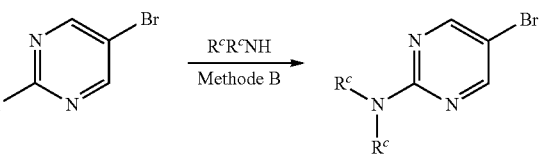

Method B) 5-Bromopyrimidin-2-yl)methylamine 5-bromo-2-chloropyrimidine (2.00 g, 10.34 mmol), methylamine (41% in water, 2.00 mL, 23.78 mmol) and potassium carbonate (1.43 g, 10.34 mmol) in tert-butanol (4 mL)/THF (4 mL) are stirred for 15 min at 150° C. in a microwave reactor. The crude mixture is diluted with DCM, the organic phase is washed with semi-saturated potassium carbonate solution and water, dried, filtered and evaporated down. Yield: 1.90 g (98%).

In the preparation of analogous components, depending on the amine chosen, it may be necessary to increase the reaction temperature or the reaction time or to add further amine to complete the reaction.

| No. | Product | Amine | Yield [%] |
|---|---|---|---|
| Z1 | | NH$_2$ ethyl | 98 |
| Z2 | | NH$_2$ cyclopropyl | 96 |
| Z3 | | NH$_2$ cyclopropylmethyl | 98 |

-continued

| No. | Product | Amine | Yield [%] |
|---|---|---|---|
| Z4 | 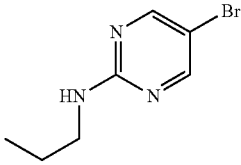 | 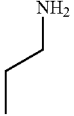 | 97 |
| Z5 | 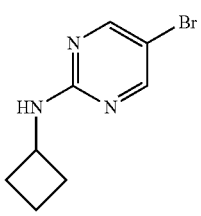 [SMILES: Brc1cnc(NC2CCC2)nc1] | 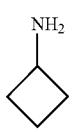 | 97 |
| Z6 | 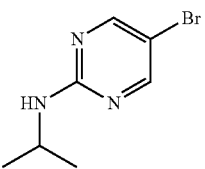 |  | 98 |
| Z7 | 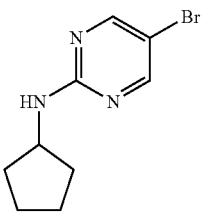 [SMILES: Brc1cnc(NC2CCCC2)nc1] | 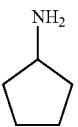 | quant. |
| Z8 | 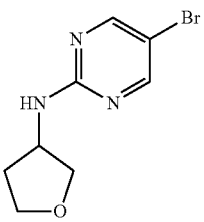 [SMILES: Brc1cnc(NC2CCOC2)nc1] | 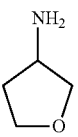 | quant. |

1.2.5. (5-Bromopyrazin-2-yl)alkylamine

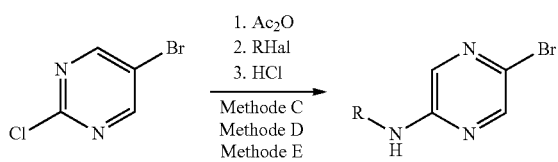

Method C) N-(5-Bromopyrazin-2-yl)acetamide

2-Amino-5-bromopyrazine (500 mg, 2.87 mmol) is stirred in acetic anhydride (5 mL) for 12 h at RT. The resulting solid is filtered off, digested with toluene and dried.

Yield: 540 mg (98%).

Method D)
N-(5-Bromopyrazin-2-yl)-N-alkylacetamide

N-(5-Bromopyrazin-2-yl)acetamide is stirred with 6-8 eq. alkylhalide and 1.5-3 eq. potassium carbonate in ACN (1 mL/100 mL educt) in a microwave reactor for 20 min at 130° C. The reaction mixture is divided between DCM and water, the organic phase is washed with water, dried, filtered and evaporated down.

| No. | Product | Alkylhalide | Yield [%] |
|---|---|---|---|
| Z9 | 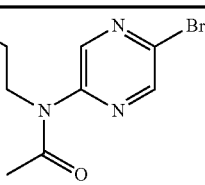 |  | 85 |
| Z10 | 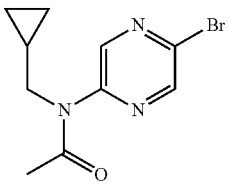 |  | quant. |
| Z11 | 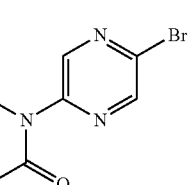 |  | quant. |

Method E) (5-Bromopyrazin-2-yl)alkylamine

N-(5-Bromopyrazin-2-yl)-N-alkylacetamide (120 mg) is stirred in water (200 μL)/conc. HCl (200 μL)/isopropanol (100 μL) in a microwave reactor for 10 min at 85° C. The reaction mixture is used directly in the next step without further purification.

1.3. Other Intermediate Compounds 1.3.1. Propynoic Acid Amides

The propynoic acid amides used are prepared analogously to the synthesis of propynoic acid —N-methylamide known from the literature (e.g. Journal of Organic Chemistry 1998, 63(15), 5050-5058) or analogously to the synthesis of propynoic acid —N— phenylamide in known from the literature (e.g. Synthetic Communications 1993, 23(14), 2003-2010).

2. Preparation of the End Compounds
2.1. Variation of the Aryl Substituent

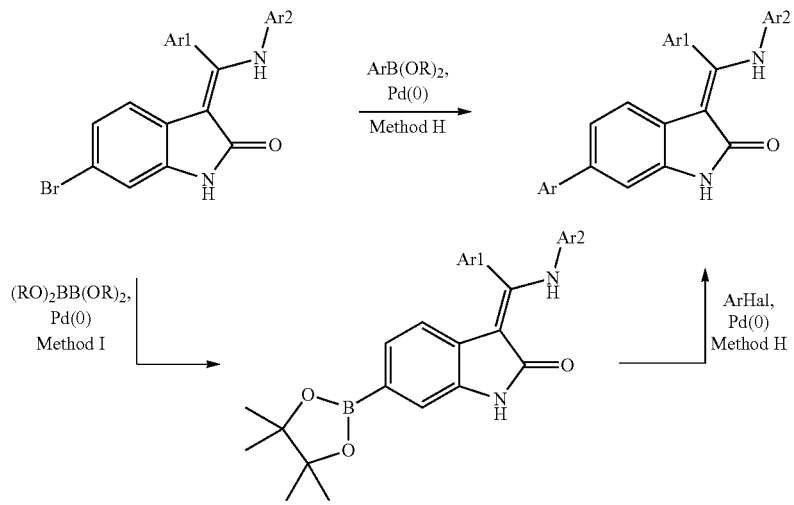

Method H) Reaction of 6-Bromoindolinone Derivatives with Arylboric Acids or Arylboric Acid Esters 6-Bromoindolinone, arylboric acid or arylboric acid ester (1.1 eq.) and tetrakis triphenylphosphine palladium (0.01-0.03 eq.) are stirred in MeOH (2 mL/1 mmol educt)/dioxane (2 mL/1 mmol educt)/2 M potassium carbonate solution (1 mL/1 mmol educt) in a microwave reactor for 10 min at 120° C. The reaction mixture is acidified with trifluoroacetic acid, filtered and purified by preparative RP-HPLC/MS.

Method I) Preparation of 6-(4,4,5,5-Tetramethyl-1.3.2-dioxaborolan-2-yl)indolinones 6-Bromoindolinone, bis(pinacolato)diboron (1.1 eq.), potassium acetate (2.0 eq.) and PdCl$_2$dppf*CH$_2$Cl$_2$ (0.02-0.03 eq.) are stirred in a mixture of anhydrous dioxane (5 mL/1 g educt) and anhydrous MeOH (5 mL/1 g educt) in a microwave reactor for 20 min at 100° C. The reaction mixture is divided between DCM and water, the organic phase is washed with water, dried, filtered and evaporated down. The crude product is optionally purified by chromatography or by crystallisation.

| No. | Product | Yield [%] |
|---|---|---|
| 1 |  | 60 |

-continued
| No. | Product | Yield [%] |
|---|---|---|
| 2 | 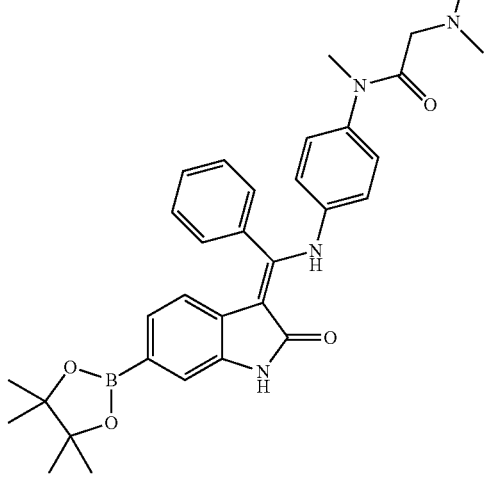 | 44 |
| 3 | 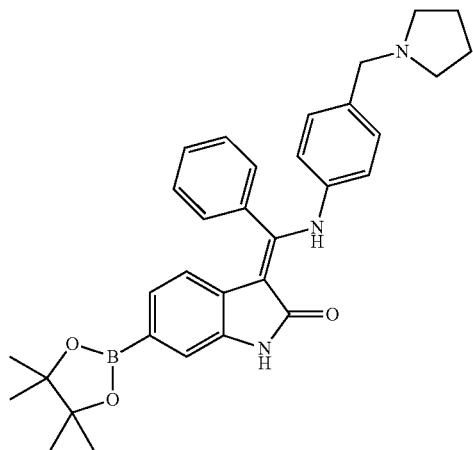 [SMILES: CC1(C)OB(c2ccc3c(c2)NC(=O)/C3=C(\Nc2ccc(CN3CCCC3)cc2)c2ccccc2)OC1(C)C] | 42 |
| 4 | 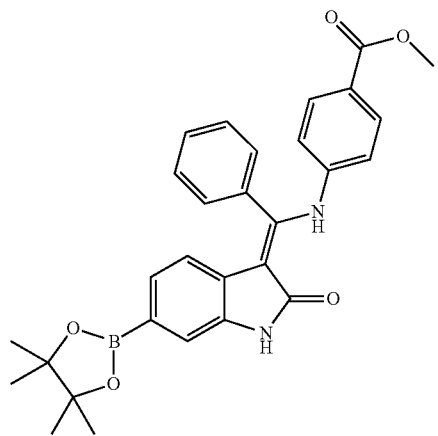 | 75 |

-continued
| No. | Product | Yield [%] |
|---|---|---|
| 5 | 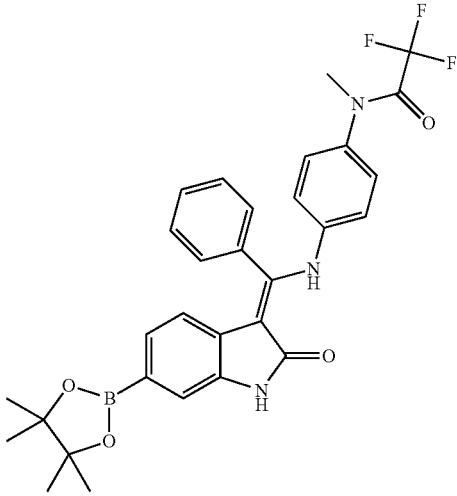 [SMILES: CN(C(=O)C(F)(F)F)c1ccc(N/C(=C2\C(=O)Nc3cc(B4OC(C)(C)C(C)(C)O4)ccc32)c2ccccc2)cc1] | 75 |
| 6 | 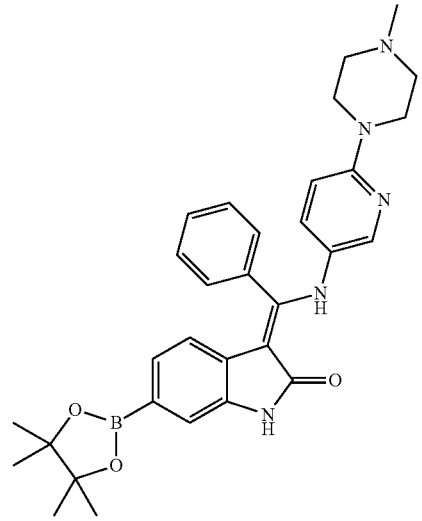 [SMILES: CN1CCN(c2ccc(N/C(=C3\C(=O)Nc4cc(B5OC(C)(C)C(C)(C)O5)ccc43)c3ccccc3)cn2)CC1] | 62 |
| 7 | 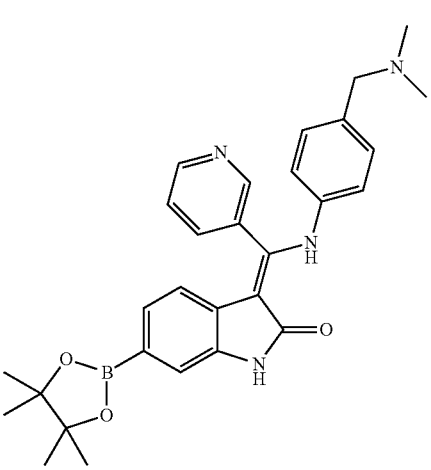 | 33 |

-continued
| No. | Product | Yield [%] |
|---|---|---|
| 8 | 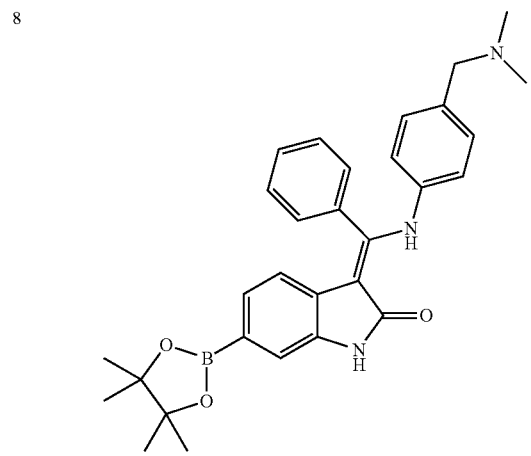 | 38 |
| 9 | 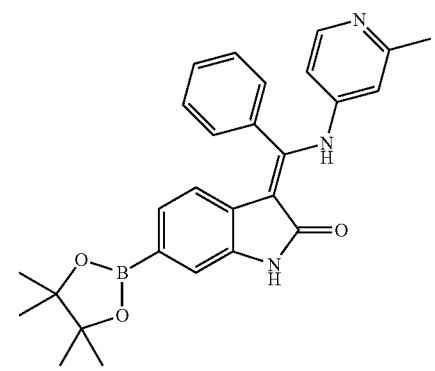 | 88 |
| 10 | 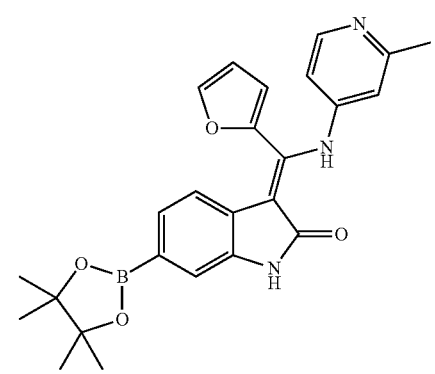 | 26 |
| 11 | 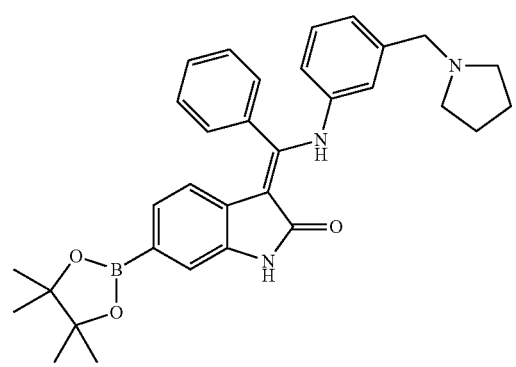 [SMILES: CC1(C)OB(c2ccc3c(c2)NC(=O)/C3=C(\Nc2cccc(CN3CCCC3)c2)c2ccccc2)OC1(C)C] | 84 |

-continued
| No. | Product | Yield [%] |
|---|---|---|
| 12 | 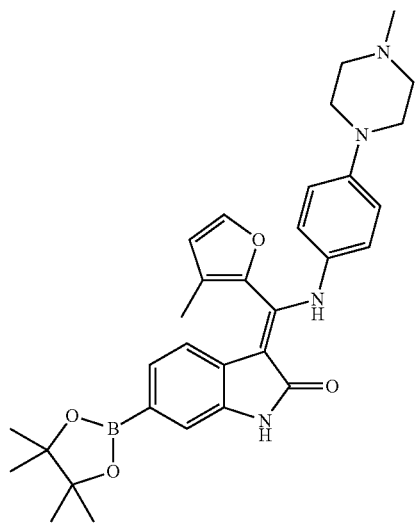 [SMILES: Cc1ccoc1/C(Nc1ccc(N2CCN(C)CC2)cc1)=C1/C(=O)Nc2cc(B3OC(C)(C)C(C)(C)O3)ccc21] | 96 |
| 13 | 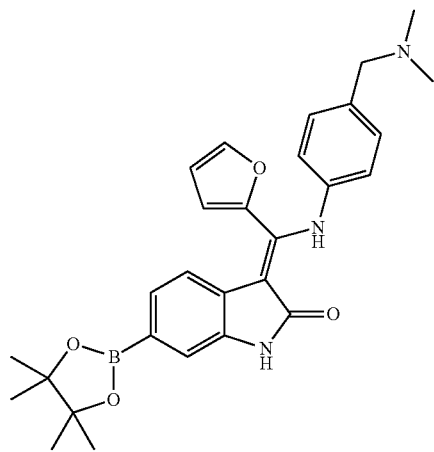 | 69 |
| 14 | 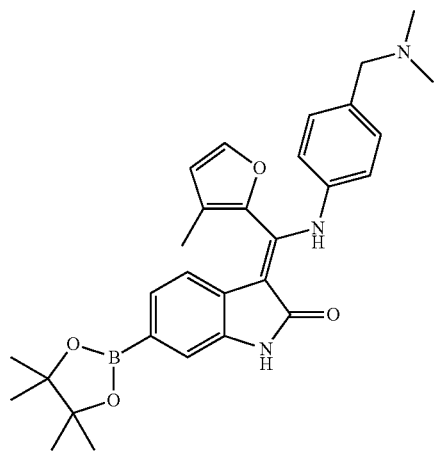 | 95 |

-continued
| No. | Product | Yield [%] |
|---|---|---|
| 15 | 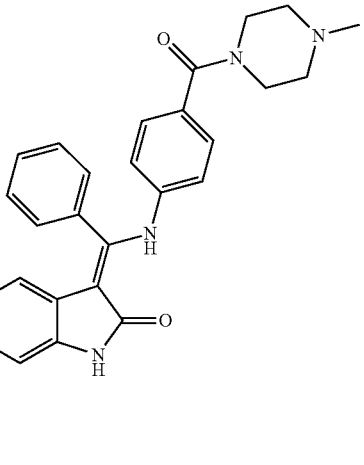 | 86 |
| 16 | 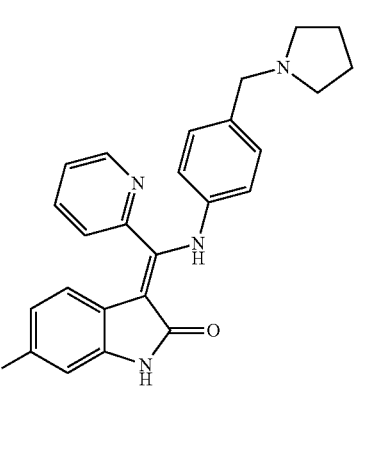 | 86 |
| 17 | 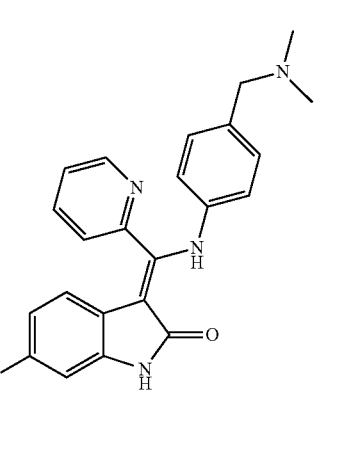 | 59 |

The reaction of indolinone-6-boric acids or -boric acid esters with arylhalides is carried out according to method H.

Examples 1-73

| No. | Aryl | $t_{ret}$ [min] | $[M + H]^+$ | $UV_{max}$ [nM] | % control (1 μM) |
|---|---|---|---|---|---|
| 1 | 5-(ethylamino)pyrazin-2-yl | 2.18 | 491 | 298 | 15.25 |
| 2 | 5-(cyclopropylmethylamino)pyrazin-2-yl | 2.25 | 517 | 296 | 12.64 |
| 3 | 3-acetylphenyl | 2.38 | 443 (fragment) | 392, 288 | 16.8 |
| 4 | 2-methylphenyl | 2.57 | 415 (fragment) | 386, 285 | 77.46 |
| 5 | 6-(ethylamino)pyridin-3-yl | 2.26 | 490 | 398, 295 | 7.08 |
| 6 | 6-(dimethylamino)pyridin-3-yl | 2.35 | 490 | 398, 297 | 11.43 |
| 7 | 6-fluoropyridin-3-yl | 2.30 | 420 (fragment) | 390, 289 | 42.8 |
| 8 | 6-(methylamino)pyridin-3-yl | 2.16 | 476 | 397, 294 | 15.61 |

-continued
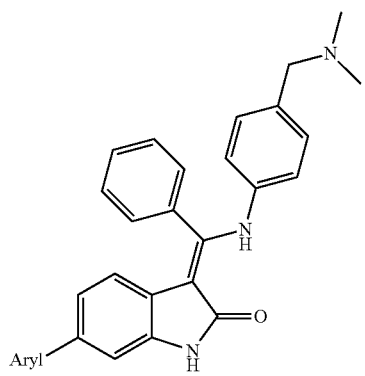
| No. | Aryl | $t_{ret}$ [min] | $[M + H]^+$ | $UV_{max}$ [nM] | % control (1 μM) |
|---|---|---|---|---|---|
| 9 | 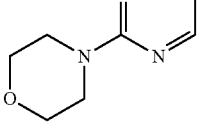 | 2.28 | 488 (fragment) | 395, 294 | 26.58 |
| 10 | 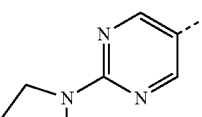 | 2.34 | 517 | 398, 295 | 10.57 |
| 11 | 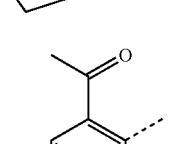 | 2.35 | 443 (fragment) | 390, 286 | 56.91 |
| 12 | 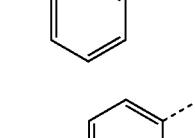 | 2.21 | 524 | 397, 311 | 40.01 |
| 13 | 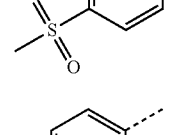 | 2.49 | 401 (fragment) | 392, 291 | 49.17 |
| 14 | 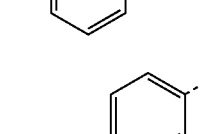 | 2.28 | 532 | 398, 295 | 20.69 |
| 15 | 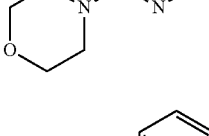 | 2.58 | 517 | 391, 288 | 21.97 |

-continued
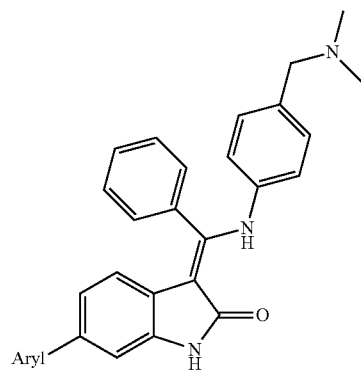
| No. | Aryl | $t_{ret}$ [min] | $[M + H]^+$ | $UV_{max}$ [nM] | % control (1 μM) |
|---|---|---|---|---|---|
| 16 | benzyl-methyl-pyrazole | 2.34 | 481 (fragment) | 396, 288 | 8.46 |
| 17 | 6-methylpyridin-3-yl | 2.20 | 461 | 390, 292 | 21.07 |
| 18 | 4-(cyanomethyl)phenyl | 2.35 | 440 (fragment) | 393, 293 | 16.62 |
| 19 | furan-2-yl | 2.38 | 391 (fragment) | 297 | 30.33 |
| 20 | 3-methylpyridin-4-yl | 2.16 | 461 | 388, 287 | 107.39 |
| 21 | 4-methoxyphenyl | 2.46 | 431 (fragment) | 393, 288 | 33.5 |
| 22 | 2-fluorophenyl | 2.49 | 419 (fragment) | 389, 289 | 32.31 |
| 23 | 2-(methanesulfonamido)phenyl | 2.23 | 539 | 385, 287 | 70.61 |

-continued
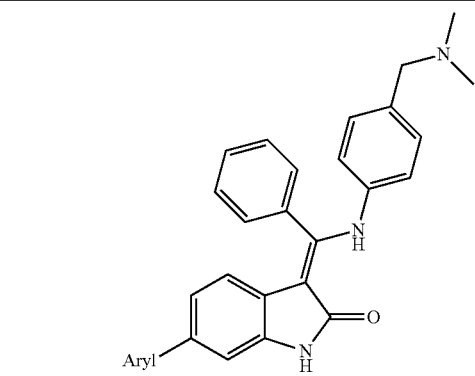
| No. | Aryl | t_ret [min] | [M + H]⁺ | UV_max [nM] | % control (1 μM) |
|---|---|---|---|---|---|
| 24 | 3-(methylsulfonylamino)phenyl | 2.19 | 494 (fragment) | 392, 293 | 31.36 |
| 25 | 4-(methylsulfonylamino)phenyl | 2.15 | 494 (fragment) | 394, 293 | 16.26 |
| 26 | 3-methylphenyl | 2.57 | 415 (fragment) | 392, 291 | 37.62 |
| 27 | 4-methylphenyl | 2.59 | 415 (fragment) | 393, 290 | 24.45 |
| 28 | 2-methoxyphenyl | 2.46 | 431 (fragment) | 389, 288 | 71.9 |
| 29 | 2-methoxypyridin-3-yl | 2.33 | 432 (fragment) | 390, 291 | 72.13 |
| 30 | furan-3-yl | 2.34 | 434 [M − H]− | 394, 289 | 60.44 |
| 31 | biphenyl-4-yl | 2.78 | 477 (fragment) | 397, 291 | 12.58 |

-continued
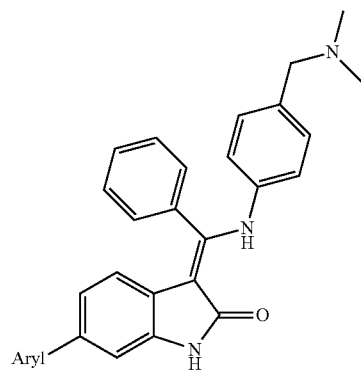
| No. | Aryl | $t_{ret}$ [min] | $[M + H]^+$ | $UV_{max}$ [nM] | % control (1 μM) |
|---|---|---|---|---|---|
| 32 | 3,5-dimethylphenyl | 2.68 | 429 (fragment) | 392, 291 | 30.56 |
| 33 | 3-carboxyphenyl | 1.75 | 445 (fragment) | 392, 291 | 92.47 |
| 34 | 2,3-dimethylphenyl | 2.63 | 429 (fragment) | 384, 283 | 112.25 |
| 35 | 4-ethylphenyl | 2.69 | 429 (fragment) | 392, 291 | 33.51 |
| 36 | 4-carboxyphenyl | 1.70 | 445 (fragment) | 394, 299 | 106.21 |
| 37 | 3-methoxyphenyl | 2.47 | 431 (fragment) | 392, 292 | 31.08 |
| 38 | 4-cyanophenyl | 2.41 | 426 (fragment) | 399, 320 | 94.38 |

-continued
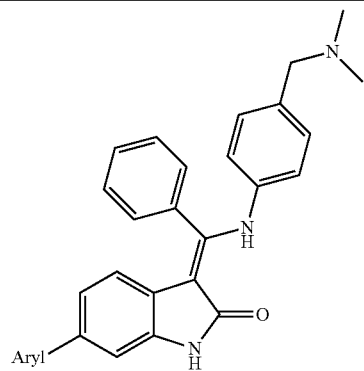
| No. | Aryl | t_ret [min] | [M + H]+ | UV_max [nM] | % control (1 μM) |
|---|---|---|---|---|---|
| 39 | 3-cyanophenyl | 2.41 | 471 | 391, 292 | 30.85 |
| 40 | quinolin-3-yl | 2.36 | 497 | 396, 275 | 34.69 |
| 41 | 5-acetylpyridin-3-yl | 2.11 | 489 | 393, 289 | 13.47 |
| 42 | 2-carboxypyrimidin-5-yl | 1.59 | 492 | 396 | 139.39 |
| 43 | 4-carbamoylphenyl | 2.01 | 489 | 395, 305 | 102.27 |
| 44 | 2-(dimethylamino)pyrimidin-5-yl | 2.32 | 491 | 396, 294 | 27.95 |
| 45 | 2-(cyclobutylamino)pyrimidin-5-yl | 2.36 | 517 | 394, 290 | 1.76 |
| 46 | 2-(isopropylamino)pyrimidin-5-yl | 2.32 | 505 | 394, 292 | 2.13 |

-continued
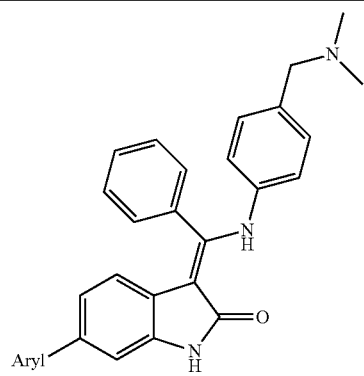
| No. | Aryl | $t_{ret}$ [min] | $[M + H]^+$ | $UV_{max}$ [nM] | % control (1 μM) |
|---|---|---|---|---|---|
| 47 | F₂CHCH₂-NH-pyrimidin-2-yl (5-yl linkage) | 2.25 | 527 | 393, 290 | 1.59 |
| 48 | cyclopropyl-NH-pyrimidin-2-yl | 2.17 | 503 | 395, 291 | 3.44 |
| 49 | FCH₂CH₂-NH-pyrimidin-2-yl | 2.17 | 507 [M − H] | 395, 291 | 3.64 |
| 50 | propyl-NH-pyrimidin-2-yl | 2.31 | 505 | 395, 292 | 2.79 |
| 51 | cyclopropylmethyl-NH-pyrimidin-2-yl | 2.34 | 517 | 395, 292 | 3.84 |
| 52 | ethyl-NH-pyrimidin-2-yl | 2.20 | 491 | 395, 292 | 2.78 |
| 53 | 4-acetylphenyl | 2.34 | 443 (fragment) | 399 | 54.29 |
| 54 | 6-carboxypyridin-3-yl | 1.64 | 491 | 397 | 156.55 |

-continued
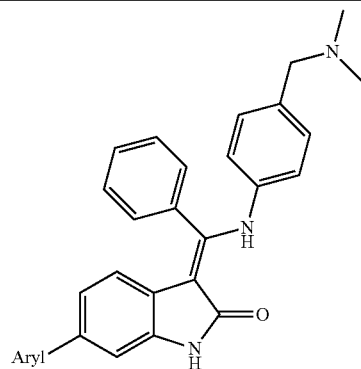
| No. | Aryl | $t_{ret}$ [min] | $[M + H]^+$ | $UV_{max}$ [nM] | % control (1 μM) |
|---|---|---|---|---|---|
| 55 | cyclopropylmethyl-NH-pyridinyl | 2.37 | 516 | 398, 294, 248 | 5.91 |
| 56 | cyclobutyl-NH-pyridinyl | 2.42 | 516 | 396, 294, 248 | 5.45 |
| 57 | propyl-NH-pyridinyl | 2.38 | 504 | 398, 292, 248 | 5.74 |
| 58 | isopropyl-NH-pyridinyl | 2.37 | 504 | 396, 294, 250 | 8.01 |
| 59 | cyclopropyl-NH-pyridinyl | 2.32 | 502 | 396, 294 | 9.19 |
| 60 | 2-oxoindolinyl | 2.06 | 501 | 395, 293 | 26.3 |
| 61 | 1H-pyrazolyl | 1.96 | 436 | 395, 287 | 14.06 |
| 62 | acetamido-pyridinyl | 2.11 | 504 | 393, 297 | 1.96 |
| 63 | methoxy-pyridinyl | 2.17 | 477 | 392, 292 | 11.02 |

-continued
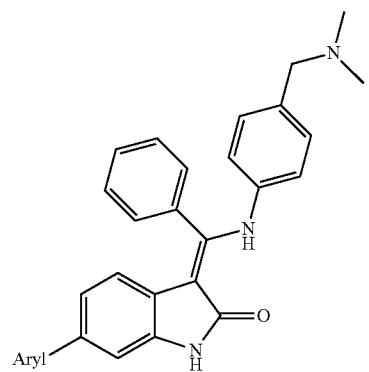
| No. | Aryl | $t_{ret}$ [min] | [M + H]$^+$ | UV$_{max}$ [nM] | % control (1 μM) |
|---|---|---|---|---|---|
| 64 | pyrazol-1-yl-phenyl | 2.43 | 512 | 392, 292 | 13.44 |
| 65 | N,N-dimethylsulfamoyl-phenyl | 2.38 | 553 | 390, 291 | 27.56 |
| 66 | 6-aminopyridin-3-yl | 2.02 | 462 | 395, 291 | 18.27 |
| 67 | sulfamoyl-phenyl | 2.11 | 525 | 392, 291 | 5.48 |
| 68 | carbamoyl-phenyl | 2.06 | 489 | 392, 291 | 18.15 |
| 69 | acetamido-phenyl | 2.16 | 503 | 392, 292 | 17.17 |

-continued
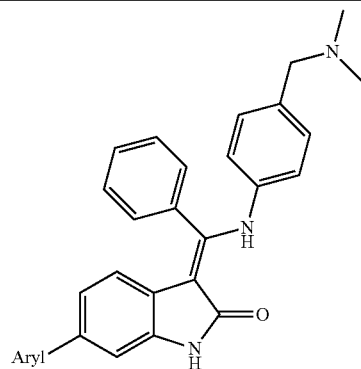
| No. | Aryl | $t_{ret}$ [min] | [M + H]⁺ | UV$_{max}$ [nM] | % control (1 μM) |
|---|---|---|---|---|---|
| 70 | 6-methoxypyridin-3-yl | 2.34 | 477 | 392, 288 | 17.26 |
| 71 | pyridin-3-yl | 2.12 | 447 | 391, 293 | 24.52 |
| 72 | 4-acetamidophenyl | 2.13 | 503 | 393, 296 | 3.37 |
The following compound is obtained analogously to the synthesis of Example 46 starting from 5-fluoro-6-bromoindolinone.
| No. | Structure | $t_{ret}$ [min] | [M + H]⁺ | UVmax [nM] | % control (1 μM) |
|---|---|---|---|---|---|
| 73 | 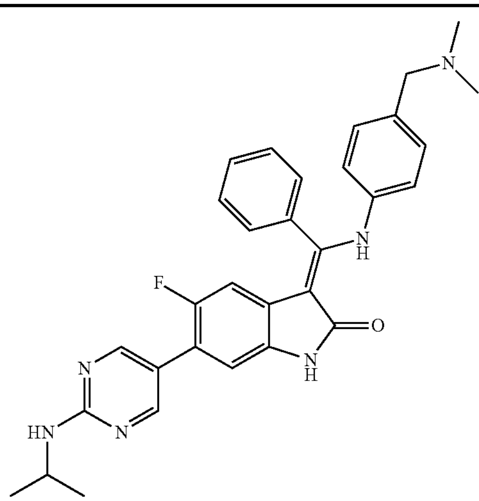 | 2.30 | 523 | 3.95 | 5.59 |

Examples 74-94
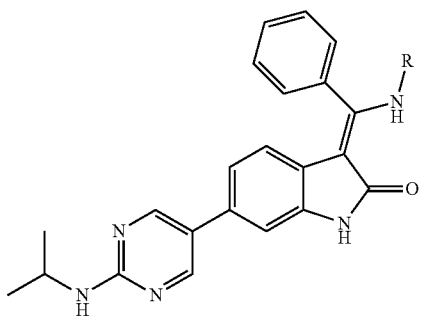
| No. | R | $t_{ret}$ [min] | $[M + H]^+$ | $UV_{max}$ [nM] | % control (1 μM) |
|---|---|---|---|---|---|
| 74 | 4-(pyrrolidin-1-ylmethyl)phenyl | 2.46 | 530 [M − H] | 396, 390 | 2.73 |
| 75 | N-methyl-N-(4-phenyl)-2-(dimethylamino)acetamide | 2.01 | 562 | 396, 291 | 1.74 |
| 76 | 4-((4-methylpiperazin-1-yl)methyl)phenyl | 2.19 | 460 (fragment) | 396, 291 | 1.96 |
| 77 | tetrahydro-2H-pyran-4-yl | 2.1 | 456 | 368, 288 | 96.23 |
| 78 | 4-(4-(cyclopropylmethyl)piperazin-1-yl)cyclohexyl | 2.27 | 592 | 368, 288 | 111.03 |
| 79 | 1-methylpiperidin-4-yl | 2.21 | 469 | 368, 288 | 103.04 |
| 80 | 2-methoxy-4-carboxyphenyl | 1.42 | 522 | 399, 292, 246 | 2.32 |
| 81 | 4-(2-carboxypropan-2-yl)phenyl | 1.62 | 534 | 395, 291 | 1.26 |

-continued

| No. | R | $t_{ret}$ [min] | $[M + H]^+$ | $UV_{max}$ [nM] | % control (1 μM) |
|---|---|---|---|---|---|
| 82 | (4-phenyl)-C(CH₃)₂-C(O)OCH₃ | 2.47 | 548 | 395, 291 | 5.13 |
| 83 | (4-phenyl)-C(O)OH | 1.44 | 492 | 398, 292 | 1.04 |
| 84 | (4-phenyl)-C(O)OCH₃ | 2.38 | 506 | 292 | 65.23 |
| 85 | (4-phenyl)-NH-CH₃ | 2.26 | 477 | 395, 291 | 50.33 |
| 86 | 5-(4-methylpiperazin-1-yl)pyridin-2-yl | 2.13 | 547 | 392, 290 | 16.81 |
| 87 | 2-methylpyridin-4-yl | 2.13 | 463 | 292 | 2.67 |
| 88 | (4-phenyl)-O-CH₂CH₂-pyrrolidin-1-yl | 2.40 | 561 | 390, 291 | 3.13 |
| 89 | (4-phenyl)-O-CH₂CH₂CH₂-N(CH₃)₂ | 2.39 | 549 | 390, 290, 244 | 5.97 |

-continued
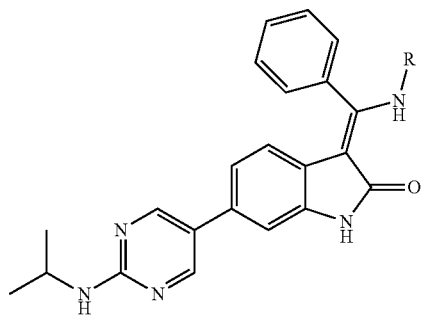
| No. | R | $t_{ret}$ [min] | $[M + H]^+$ | $UV_{max}$ [nM] | % control (1 μM) |
|---|---|---|---|---|---|
| 90 | 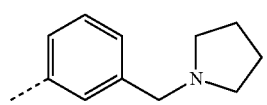 | 2.56 | 545 | 395, 291 | 3.77 |
| 91 | 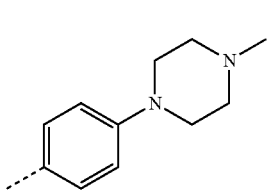 | 2.40 | 531 | 392, 292 | 9.48 |
| 92 | 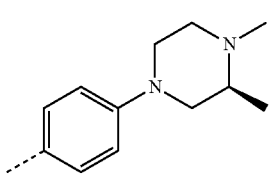 | 1.94 | 546.3 | 291 | 3.85 |
| 93 | 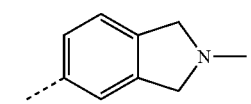 | 1.98 | 560.3 | 291 | 2.92 |
| 94 |  | 1.88 | 503 | 393, 290 | 5.83 |

Examples 95-98
| No. | HetAr | Aryl | $t_{ret}$ [min] | $[M+H]^+$ | $UV_{max}$ [nM] | % control (1 μM) |
|---|---|---|---|---|---|---|
| 95 | furan-2-yl | 4-((dimethylamino)methyl)phenyl | 2.03 | 494 | 293 | 2.27 |
| 96 | 3-methylfuran-2-yl | 4-((dimethylamino)methyl)phenyl | 2.06 | 508 | 296 | 4.28 |
| 97 | pyridin-2-yl | 4-(pyrrolidin-1-ylmethyl)phenyl | 1.97 | 531 | 395, 296 | 5.77 |
| 98 | pyridin-4-yl | 4-((dimethylamino)methyl)phenyl | 1.80 | 505 | 393, 301 | 10.92 |
2.2. Amide Syntheses
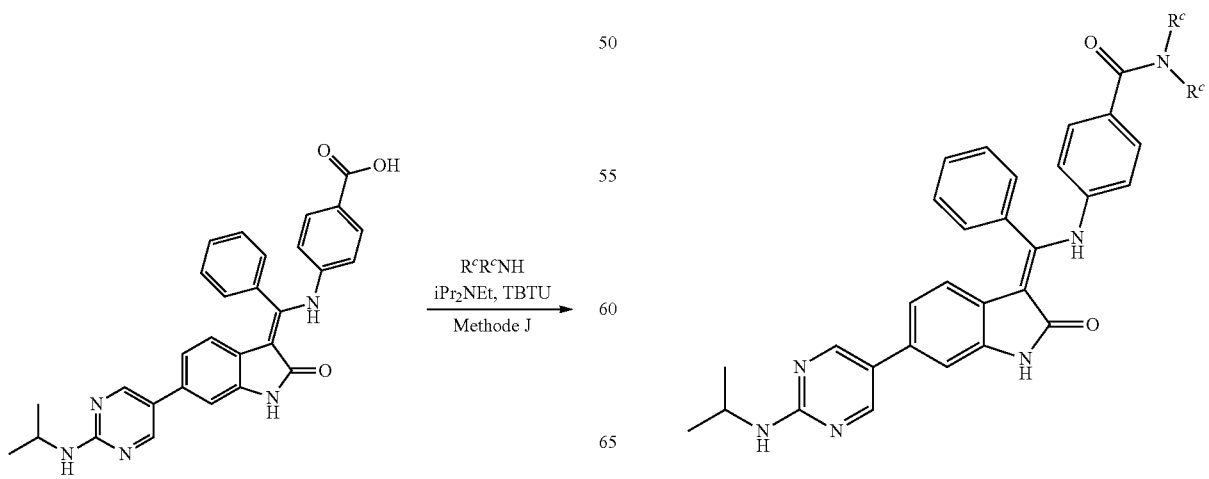

Method J) Reaction of Carboxylic Acids to Form Carboxamides

Triethylamine (3.0 equivalents) is added to a solution of the carboxylic acid and TBTU (1.3 equivalents) in anhydrous DMSO or NMP (5-7 µL/1 mg carboxylic acid) and stirred for 15 min at RT. The amine (1.5 equivalents) is added and stirred for 1 h at RT. The reaction mixture is acidified with trifluoroacetic acid, filtered and purified by preparative RP-HPLC/MS.

Examples 99-140

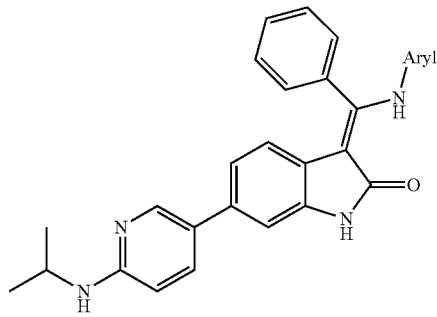

| No. | Aryl | $t_{ret}$ [min] | $[M + H]^+$ | $UV_{max}$ [nM] | % control (1 µM) |
|---|---|---|---|---|---|
| 99 | 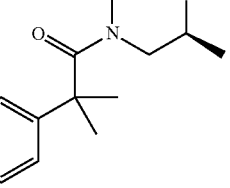 | 2.14 | 616 | 394, 292, 246 | 4.64 |
| 100 | 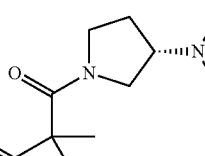 | 2.20 | 630 | 396, 292, 246 | 3.36 |
| 101 | 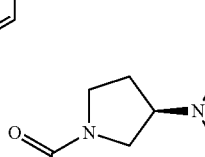 | 2.20 | 630 | 394, 292, 246 | 3.62 |
| 102 | 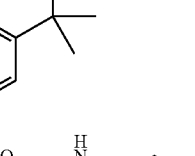 | 2.22 | 630 | 396, 290, 244 | 2.07 |
| 103 | 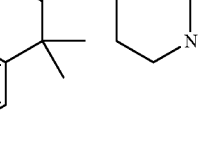 | 2.26 | 644 | 397, 292 | 3.84 |

-continued
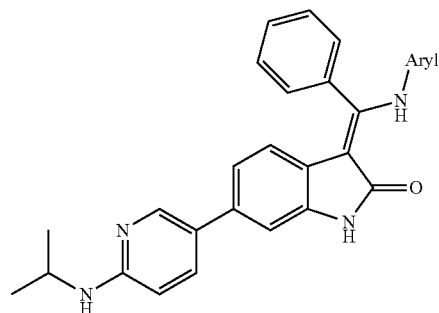
| No. | Aryl | $t_{ret}$ [min] | $[M + H]^+$ | $UV_{max}$ [nM] | % control (1 μM) |
|---|---|---|---|---|---|
| 104 | | 2.23 | 658 | 399, 292 | 1.71 |
| 105 | | 2.07 | 618 | 399, 292 | 1.57 |
| 106 | | 2.22 | 632 | 399, 292 | 2.94 |
| 107 | | 2.14 | 632 | 399, 291 | 1.66 |
| 108 | | 2.00 | 616 | 399, 292 | 1.45 |
| 109 | | 2.06 | 604 | 399, 292 | 2.08 |

-continued
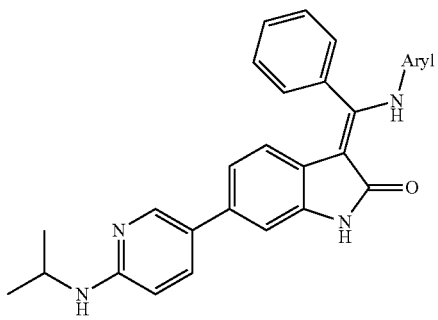
| No. | Aryl | $t_{ret}$ [min] | $[M + H]^+$ | $UV_{max}$ [nM] | % control (1 μM) |
|---|---|---|---|---|---|
| 110 | | 2.07 | 618 | 399, 292 | 1.54 |
| 111 | | 2.11 | 606 | 399, 292 | 2.35 |
| 112 | | 2.09 | 632 | 399, 291 | 1.7 |
| 113 | | 1.16 | 588 | 399, 291 | 4.25 |
| 114 | | 2.47 | 616 | 399, 291 | 7.11 |
| 115 | | 1.99 | 574 | 398, 292 | 3.25 |

-continued
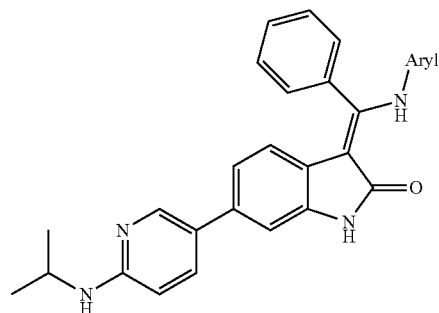
| No. | Aryl | $t_{ret}$ [min] | $[M + H]^+$ | $UV_{max}$ [nM] | % control (1 μM) |
| --- | --- | --- | --- | --- | --- |
| 116 | | 2.13 | 614 | 399, 291 | 3.16 |
| 117 | | 2.22 | 628 | 398, 291 | 3.03 |
| 118 | | 2.24 | 614 | 399, 292 | 4.44 |
| 119 | | 2.26 | 614 | 399, 292 | 3.54 |
| 120 | | 2.06 | 588 | 399, 292 | 2.75 |
| 121 | | 2.06 | 644 | 399, 292 | 3.31 |

-continued

| No. | Aryl | t_ret [min] | [M + H]⁺ | UV_max [nM] | % control (1 μM) |
|---|---|---|---|---|---|
| 122 | (4-[4-(pyrrolidin-1-yl)piperidin-1-yl]carbonylphenyl) | 2.25 | 628 | 399, 292 | 4 |
| 123 | (4-[4-isopropylpiperazin-1-yl]carbonylphenyl) | 2.21 | 602 | 399, 292 | 2.69 |
| 124 | (4-[(3,5-dimethylpiperazin-1-yl)carbonyl]phenyl) | 2.05 | 588 | 399, 292 | 3.38 |
| 125 | (4-[4-(2,2,2-trifluoroethyl)piperazin-1-yl]carbonylphenyl) | 2.34 | 642 | 399, 291 | 8.83 |
| 126 | (4-[4-cyclopropylpiperazin-1-yl]carbonylphenyl) | 2.24 | 600 | 399, 292 | 5.84 |
| 127 | (4-[(2S)-2-(pyrrolidin-1-ylmethyl)pyrrolidin-1-yl]carbonylphenyl) | 2.33 | 628 | 399, 292 | 4.67 |

-continued
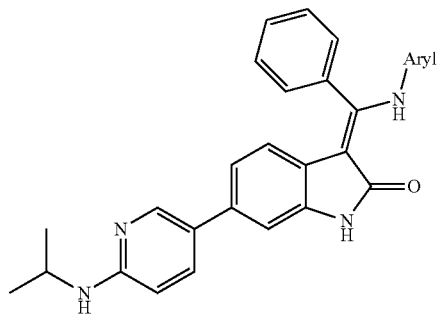
| No. | Aryl | t_ret [min] | [M + H]+ | UV_max [nM] | % control (1 μM) |
|---|---|---|---|---|---|
| 128 | | 2.11 | 602 | 399, 292 | 4.34 |
| 129 | | 2.06 | 644 | 292 | 4.55 |
| 130 | | 2.33 | 628 | 398, 292 | 1.43 |
| 131 | | 1.99 | 586 | 399, 293 | 5.48 |
| 132 | | 1.95 | 560 | 399, 292 | 0.52 |
| 133 | | 2.00 | 574 | 397, 293 | 0.55 |

-continued
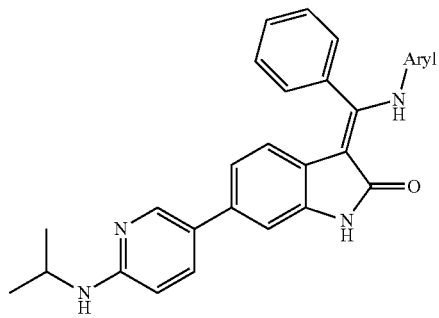
| No. | Aryl | t_ret [min] | [M + H]+ | UV_max [nM] | % control (1 μM) |
|---|---|---|---|---|---|
| 134 | | 2.10 | 562 | 399, 292 | 1.43 |
| 135 | | 2.05 | 574 | 399, 291 | 0.77 |
| 136 | | 2.07 | 588 | 399, 292 | 0.48 |
| 137 | | 2.08 | 588 | 399, 292 | 0.67 |
| 138 | | 2.10 | 576 | 398, 292 | 0.68 |
| 139 | | 2.11 | 602 | 399, 291 | 0.88 |
| 140 | | 2.13 | 588 | 399, 292 | 2.26 |

2.3. Synthesis of Aminoacetamide Derivatives

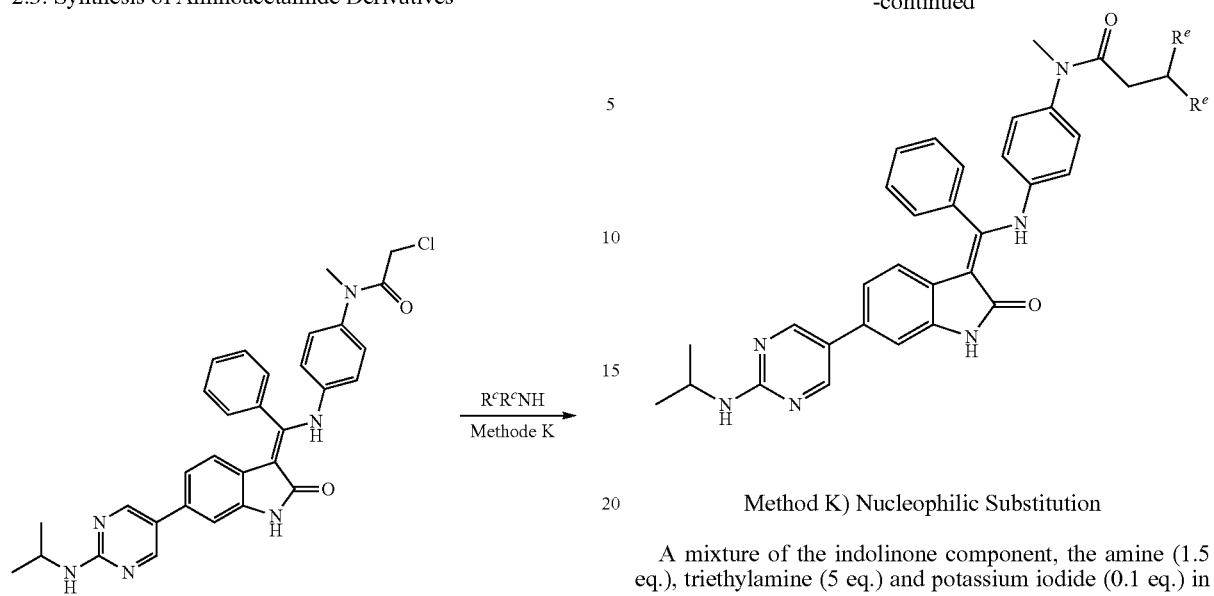

Method K) Nucleophilic Substitution

A mixture of the indolinone component, the amine (1.5 eq.), triethylamine (5 eq.) and potassium iodide (0.1 eq.) in NMP (5 mL/g indolinone) is stirred for 6 min at 150° C. in a microwave reactor. The reaction mixture is acidified with trifluoroacetic acid, filtered and purified by preparative RP-HPLC/MS.

Examples 141-150

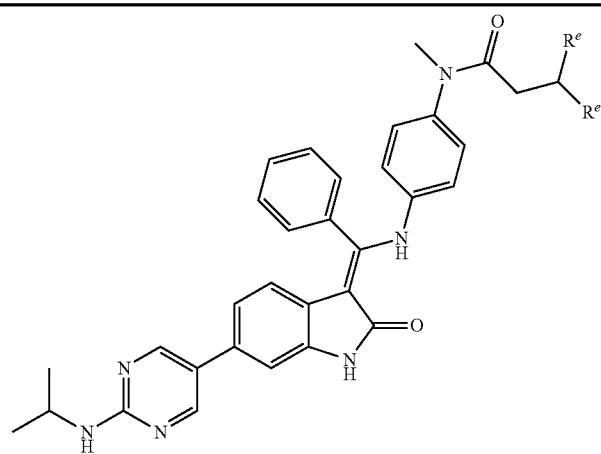

| No. | $NR^eR^e$ | $t_{ret}$ [min] | $[M + H]^+$ | $UV_{max}$ [nM] | % control (1 µM) |
|---|---|---|---|---|---|
| 141 | 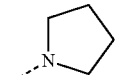 | 2.21 | 588 | 396, 292 | 0.98 |
| 142 | 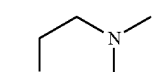 | 2.06 | 617 | 396, 291 | 1.66 |
| 143 | 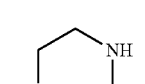 | 2.06 | 617 | 394, 292 | 2.34 |
| 144 | 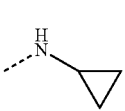 | 2.15 | 574 | 396, 291 | 0.94 |

-continued
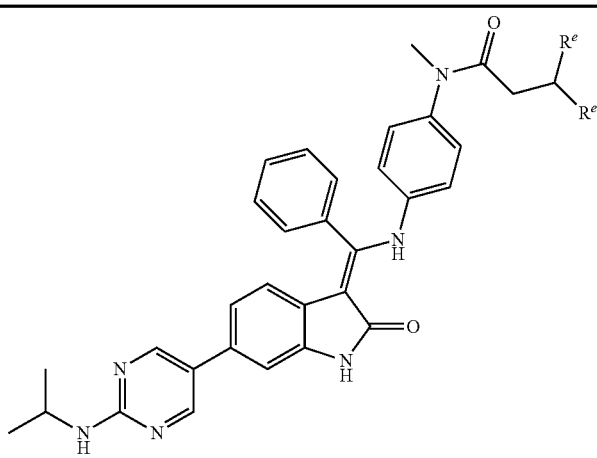
| No. | NR$^e$R$^e$ | t$_{ret}$ [min] | [M + H]$^+$ | UV$_{max}$ [nM] | % control (1 μM) |
|---|---|---|---|---|---|
| 145 | | 2.18 | 631 | 398, 292 | 1.71 |
| 146 | | 2.08 | 604 | 396, 291 | 0.99 |
| 147 | | 2.26 | 590 | 395, 291 | 0.81 |
| 148 | | 2.04 | 603 | 396, 291 | 2 |
| 149 | | 2.17 | 576 | 396, 292 | 1.15 |
| 150 | | 2.13 | 631 | 397, 292 | 1.45 |

2.4. Synthesis of Examples 151-158—General Method

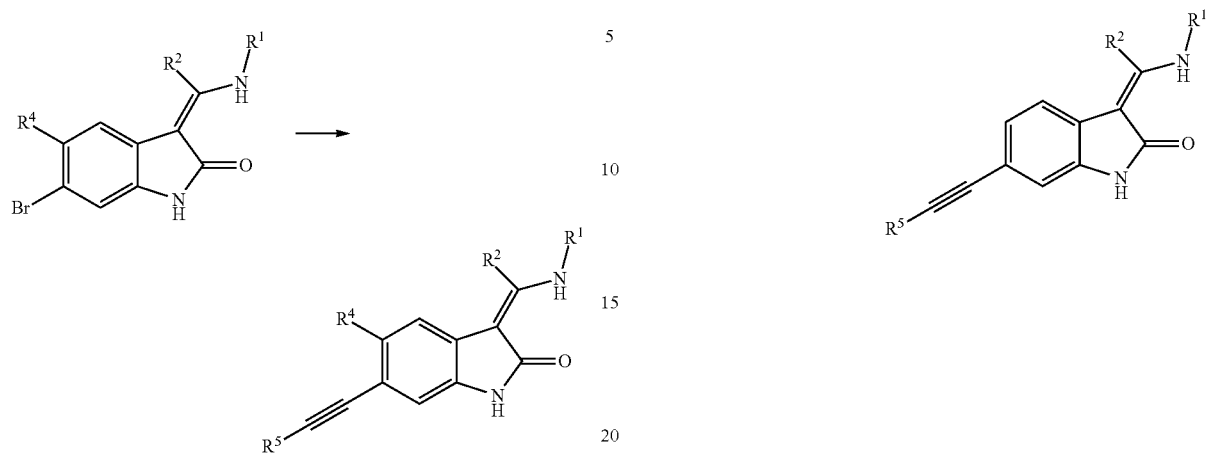

The correspondingly substituted 6-bromoindolinone (92 µmol) is combined under argon with the corresponding alkyne (360 µmol), CuI (18 µmol), 0.5 mL NMP or DMSO, 93 µL triethylamine and Pd(PPh$_3$)$_2$Cl$_2$ (9 µmol). The mixture is heated to 80-100° C. and stirred for 1-12 h until the desired product has formed. The product is isolated by RP chromatography.

2.5. Synthesis of Examples 159-177—General Method

The correspondingly substituted 6-bromoindolinone (134 µmol) is combined under argon with tert-butyldiphenylphosphine (27 µmol), 1,1,3,3-tetramethylguanidine (202 µmol), 600 µL NMP and tris(dibenzylideneacetone)dipalladium(0) (13 µmol). The reaction mixture is heated to 85° C. and after a few minutes a mixture of 403 µmol of the corresponding alkyne, 300 µL NMP and 1,1,3,3-tetramethylguanidine (404 µmol) is slowly added dropwise. The mixture is stirred until product has formed, cooled to RT, diluted with ACN and neutralised with 1 N HCl. The volatile constituents are removed and the product is isolated by RP chromatography.

Examples 151-177

| No. | Structure | $t_{ret}$ [min] | [M + H]$^+$ | UVmax [nM] | % control (1 µM) |
|---|---|---|---|---|---|
| 151 | 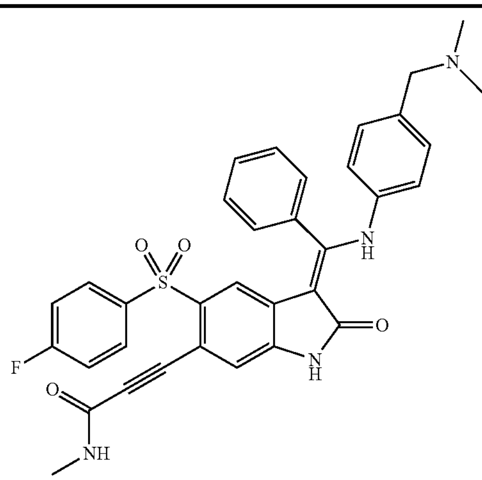 | 2.12 | 609 | 401 | 1.89 |

-continued

| No. | Structure | $t_{ret}$ [min] | $[M+H]^+$ | UVmax [nM] | % control (1 μM) |
|---|---|---|---|---|---|
| 152 | 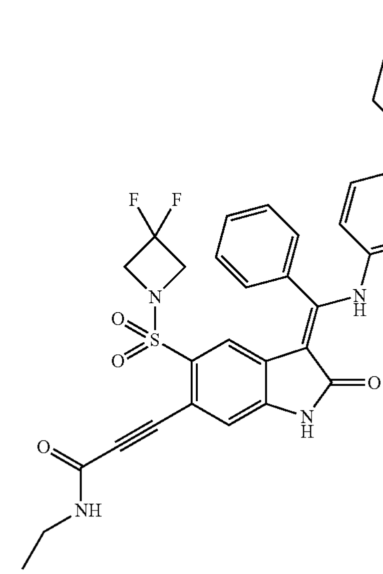 | 2.06 | 661 | 401 | 4.33 |
| 153 | 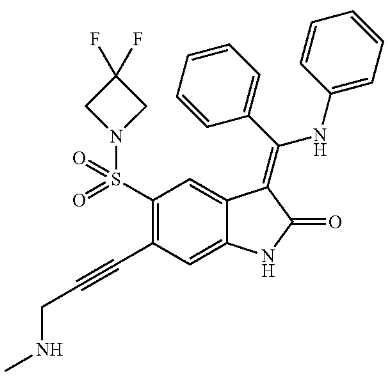 [SMILES: CNCC#Cc1cc2c(cc1S(=O)(=O)N1CC(F)(F)C1)/C(=C(/Nc1ccccc1)c1ccccc1)C(=O)N2] | 2.13 | 535 | 387 | 1.2 |
| 154 | 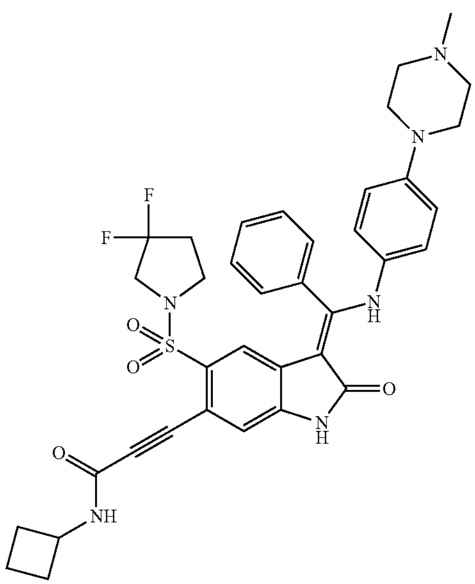 [SMILES: CN1CCN(c2ccc(N/C(=C3\C(=O)Nc4cc(C#CC(=O)NC5CCC5)c(S(=O)(=O)N5CCC(F)(F)C5)cc43)c3ccccc3)cc2)CC1] | 2.18 | $[M-H]^-$ 699 | 405 | 2.62 |

-continued

| No. | Structure | t_ret [min] | [M + H]+ | UVmax [nM] | % control (1 μM) |
|---|---|---|---|---|---|
| 155 | 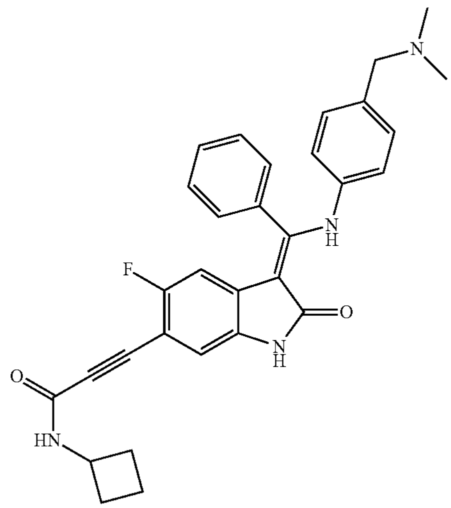 [SMILES: CN(C)Cc1ccc(N/C(=C2\C(=O)Nc3cc(C#CC(=O)NC4CCC4)c(F)cc32)c2ccccc2)cc1] | 2.27 | 509 | 390 | 8.61 |
| 156 | 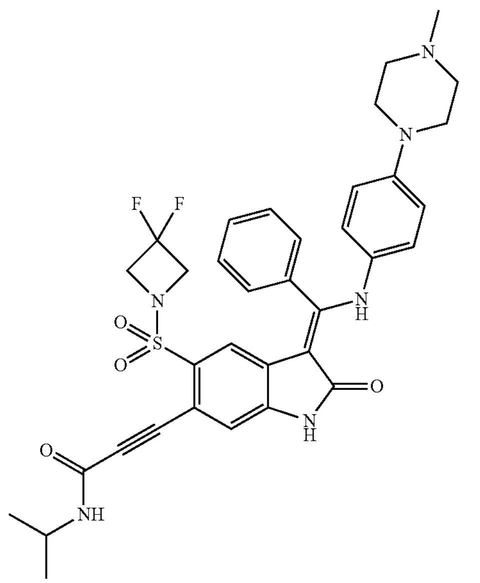 [SMILES: CC(C)NC(=O)C#Cc1cc2c(cc1S(=O)(=O)N1CC(F)(F)C1)/C(=C(/Nc1ccc(N3CCN(C)CC3)cc1)c1ccccc1)C(=O)N2] | 2.13 | 675 | 402 | 3.02 |
| 157 | 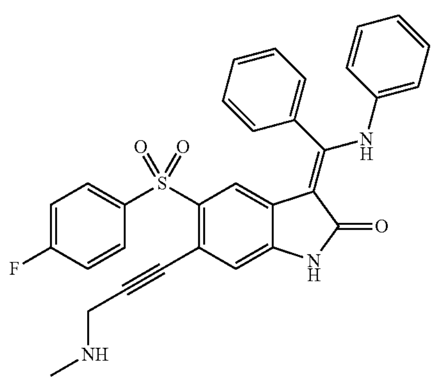 [SMILES: CNCC#Cc1cc2c(cc1S(=O)(=O)c1ccc(F)cc1)/C(=C(/Nc1ccccc1)c1ccccc1)C(=O)N2] | 2.17 | 538 | 390 | 1.98 |

-continued

| No. | Structure | $t_{ret}$ [min] | $[M + H]^+$ | UVmax [nM] | % control (1 μM) |
|---|---|---|---|---|---|
| 158 | 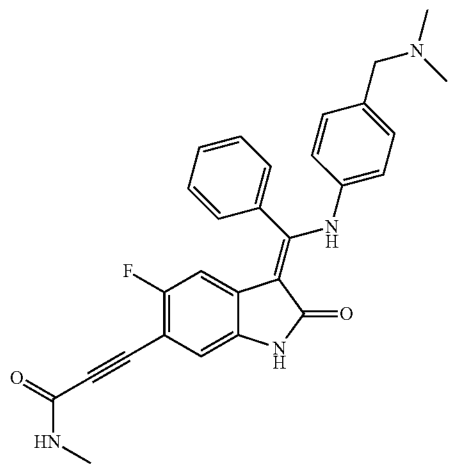 [SMILES: CNC(=O)C#Cc1cc2c(cc1F)/C(=C(/Nc1ccc(CN(C)C)cc1)c1ccccc1)C(=O)N2] | 2.06 | 469 | 396 | 7.53 |
| 159 | 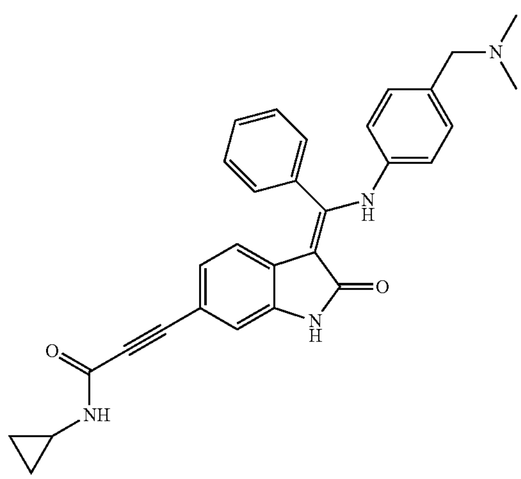 [SMILES: CN(C)Cc1ccc(N/C(=C2\C(=O)Nc3cc(C#CC(=O)NC4CC4)ccc32)c2ccccc2)cc1] | 1.86 | 477 | 396 | 2.07 |
| 160 | 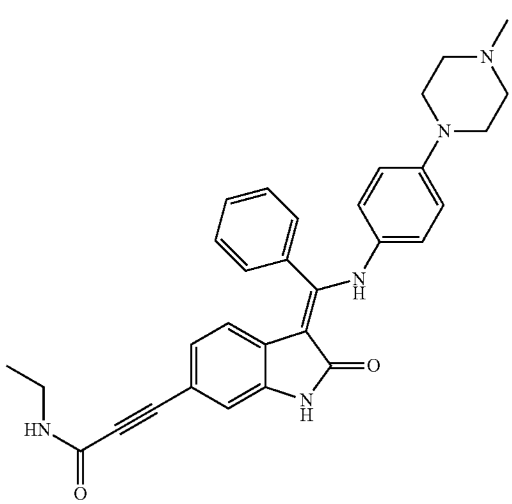 [SMILES: CCNC(=O)C#Cc1ccc2c(c1)NC(=O)/C2=C(\Nc1ccc(N2CCN(C)CC2)cc1)c1ccccc1] | 1.78 | 506 | 402 | 1.39 |

-continued

| No. | Structure | $t_{ret}$ [min] | [M + H]$^+$ | UVmax [nM] | % control (1 μM) |
|---|---|---|---|---|---|
| 161 | 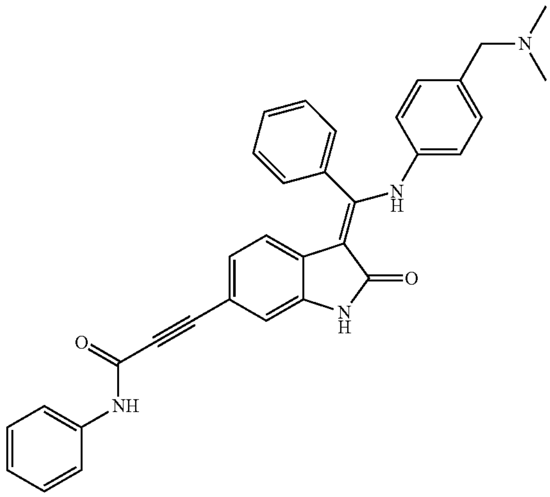 [SMILES: CN(C)Cc1ccc(N/C(=C2\C(=O)Nc3cc(C#CC(=O)Nc4ccccc4)ccc32)c2ccccc2)cc1] | 2.08 | 513 | | 1.69 |
| 162 | 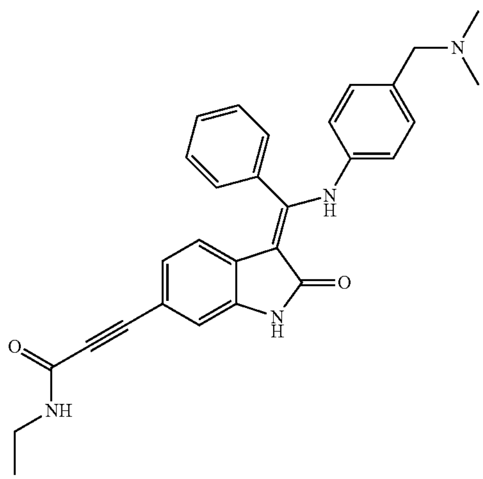 [SMILES: CCNC(=O)C#Cc1ccc2c(c1)NC(=O)/C2=C(\Nc1ccc(CN(C)C)cc1)c1ccccc1] | 1.82 | 465 | 396 | 1.65 |
| 163 | 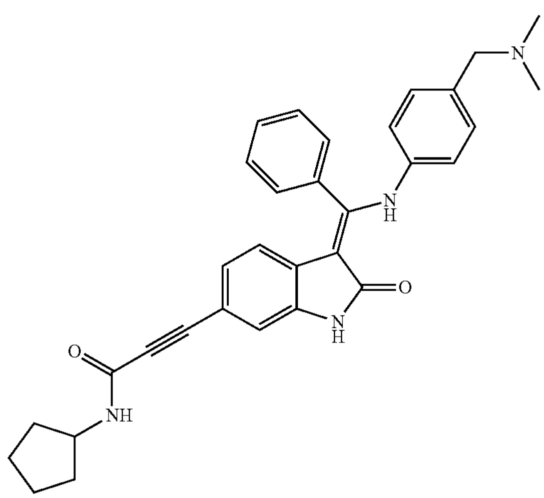 [SMILES: CN(C)Cc1ccc(N/C(=C2\C(=O)Nc3cc(C#CC(=O)NC4CCCC4)ccc32)c2ccccc2)cc1] | 2.03 | 505 | 398 | 2.08 |

-continued

| No. | Structure | $t_{ret}$ [min] | $[M + H]^+$ | UVmax [nM] | % control (1 μM) |
|---|---|---|---|---|---|
| 164 | 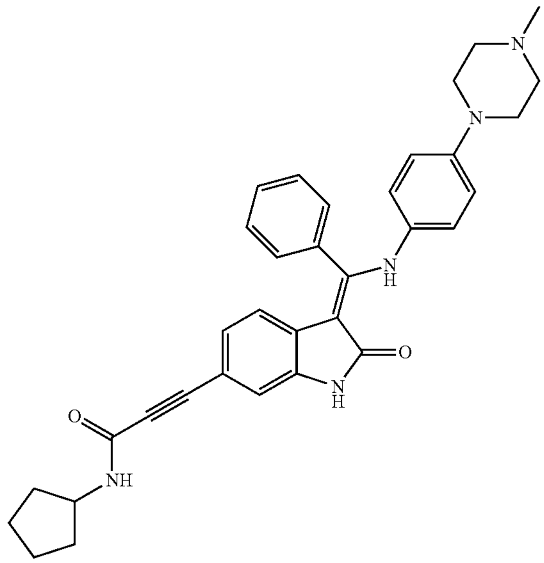 [SMILES: CN1CCN(c2ccc(N/C(=C3\C(=O)Nc4cc(C#CC(=O)NC5CCCC5)ccc43)c3ccccc3)cc2)CC1] | 1.96 | 546 | 402 | 3.17 |
| 165 | 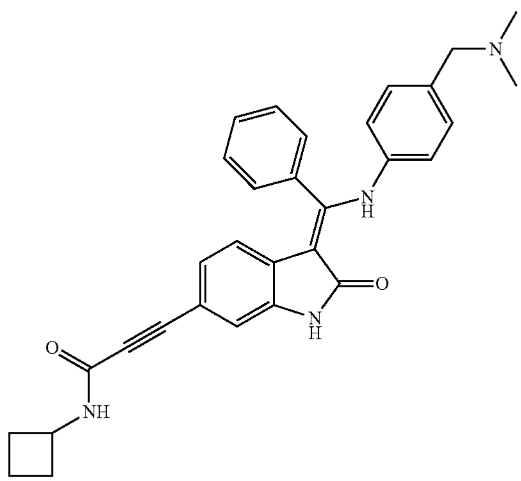 [SMILES: CN(C)Cc1ccc(N/C(=C2\C(=O)Nc3cc(C#CC(=O)NC4CCC4)ccc32)c2ccccc2)cc1] | 1.96 | 491 | 397 | 2.4 |
| 166 | 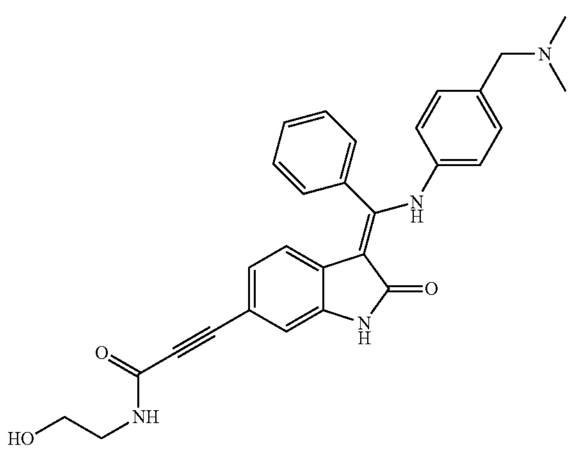 [SMILES: CN(C)Cc1ccc(N/C(=C2\C(=O)Nc3cc(C#CC(=O)NCCO)ccc32)c2ccccc2)cc1] | 1.65 | 481 | 396 | 1.93 |

-continued

| No. | Structure | $t_{ret}$ [min] | $[M+H]^+$ | UVmax [nM] | % control (1 μM) |
|---|---|---|---|---|---|
| 167 | 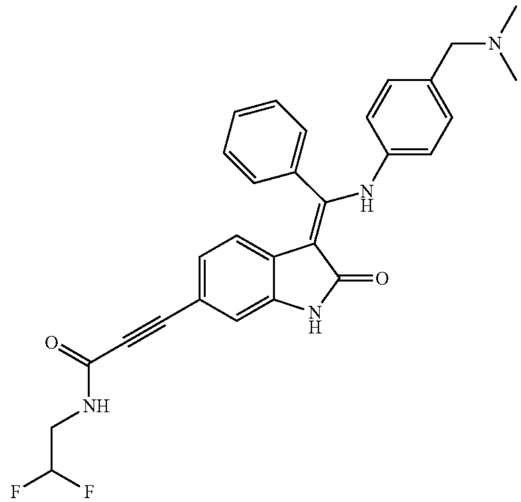 [SMILES: CN(C)Cc1ccc(N/C(=C2\C(=O)Nc3cc(C#CC(=O)NCC(F)F)ccc32)c2ccccc2)cc1] | 1.89 | 501 | 398 | 2.96 |
| 168 | 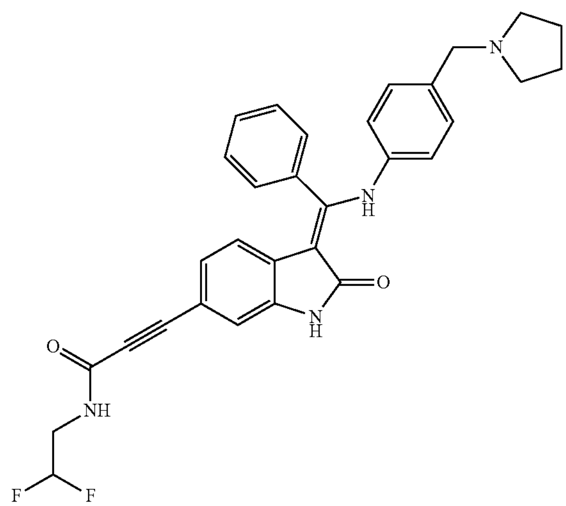 [SMILES: O=C(C#Cc1ccc2c(c1)NC(=O)/C2=C(\Nc1ccc(CN2CCCC2)cc1)c1ccccc1)NCC(F)F] | 2.06 | 527 | 398 | 1.85 |
| 169 | 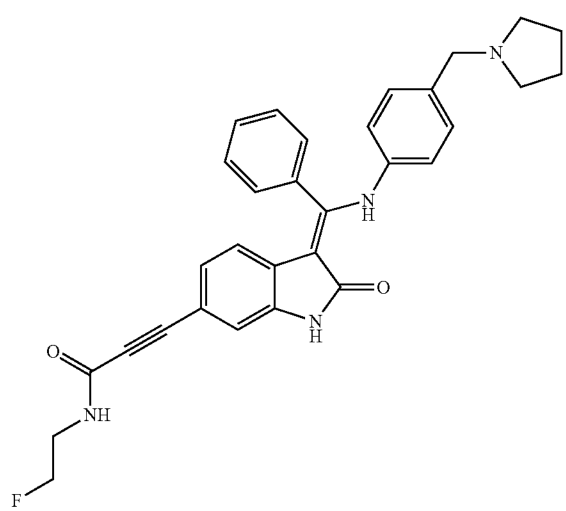 [SMILES: O=C(C#Cc1ccc2c(c1)NC(=O)/C2=C(\Nc1ccc(CN2CCCC2)cc1)c1ccccc1)NCCF] | 1.98 | 509 | 398 | 1.71 |

-continued

| No. | Structure | t_ret [min] | [M + H]+ | UVmax [nM] | % control (1 μM) |
|---|---|---|---|---|---|
| 170 | 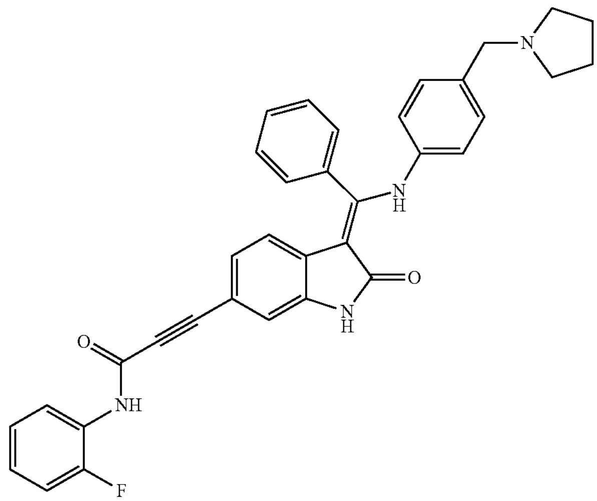 [SMILES: O=C(C#Cc1ccc2c(c1)NC(=O)/C2=C(\Nc1ccc(CN2CCCC2)cc1)c1ccccc1)Nc1ccccc1F] | 2.26 | 557 | 401 | 1.39 |
| 171 | Chiral | 1.71 | 495 | 396 | 3.39 |
| 172 | Chiral | 1.84 | 521 | 396 | 3.21 |

-continued
| No. | Structure | $t_{ret}$ [min] | $[M + H]^+$ | UVmax [nM] | % control (1 μM) |
|---|---|---|---|---|---|
| 173 | 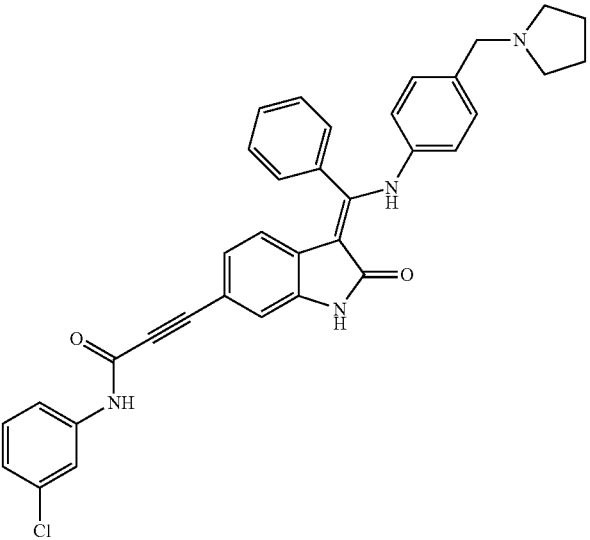 [SMILES: O=C(C#Cc1ccc2c(c1)NC(=O)/C2=C(\Nc1ccc(CN2CCCC2)cc1)c1ccccc1)Nc1cccc(Cl)c1] | 2.37 | $[M - H]^-$ 571 | 402 | 3.68 |
| 174 | 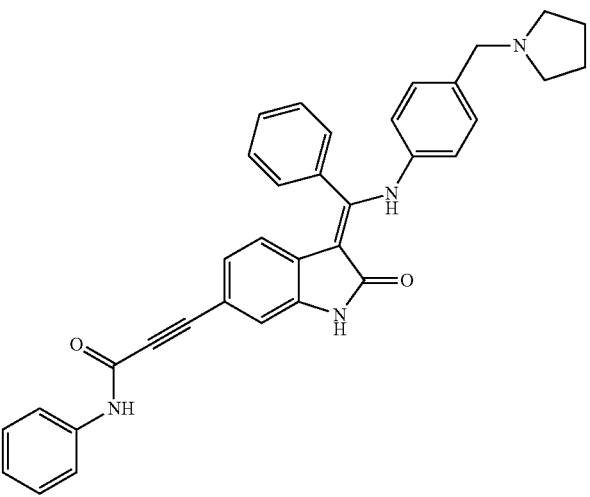 [SMILES: O=C(C#Cc1ccc2c(c1)NC(=O)/C2=C(\Nc1ccc(CN2CCCC2)cc1)c1ccccc1)Nc1ccccc1] | 2.23 | $[M - H]^-$ 537 | 400 | 2.67 |
| 175 | 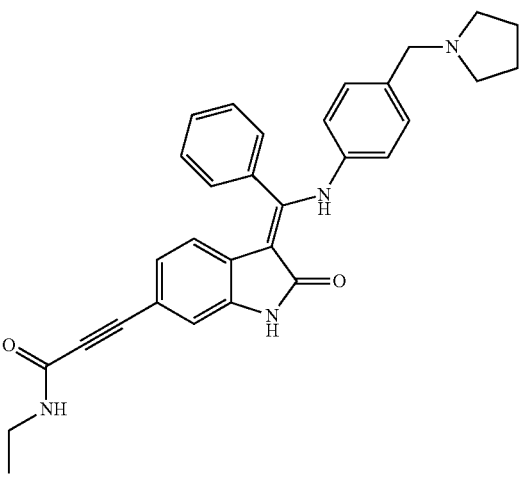 [SMILES: CCNC(=O)C#Cc1ccc2c(c1)NC(=O)/C2=C(\Nc1ccc(CN2CCCC2)cc1)c1ccccc1] | 1.73 | 491 | 396 | 3.04 |

| No. | Structure | $t_{ret}$ [min] | [M + H]$^+$ | UVmax [nM] | % control (1 μM) |
|---|---|---|---|---|---|
| 176 | 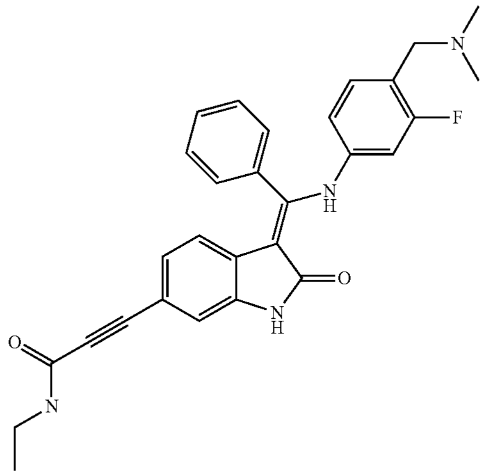 [SMILES: CCNC(=O)C#Cc1ccc2c(c1)NC(=O)/C2=C(\Nc1ccc(CN(C)C)c(F)c1)c1ccccc1] | 1.99 | 483 | 398 | 1.65 |
| 177 | 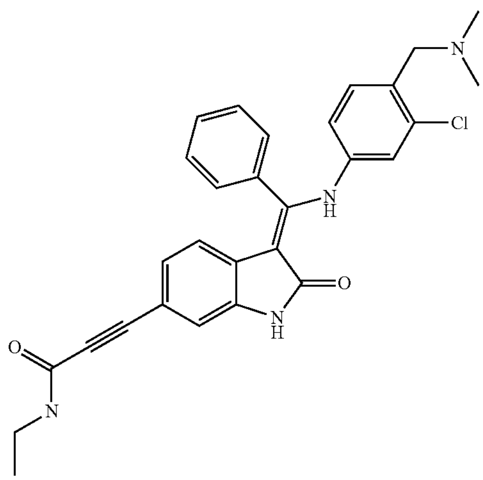 [SMILES: CCNC(=O)C#Cc1ccc2c(c1)NC(=O)/C2=C(\Nc1ccc(CN(C)C)c(Cl)c1)c1ccccc1] | 2.11 | 499/501 | 398 | 1.83 |

3. Abbreviations Used

| | |
|---|---|
| ACN | acetonitrile |
| eq. | equivalent(s) |
| DCM | dichloromethane |
| DMSO | dimethylsulphoxide |
| dppf | 1,1'-bis(diphenylphosphino)ferrocene |
| EtOAc | ethyl acetate |
| iPr$_2$NEt | diisopropylethylamine (Hünig base) |
| h | hour(s) |
| HCl | hydrochloric acid |
| HPLC | high performance liquid chromatography |
| conc. | concentrated |
| iPrOH | isopropanol |
| M | molar |
| MeOH | methanol |
| min | minute(s) |
| mL | millilitre(s) |
| MS | mass spectrometry |
| N | normal |
| NMP | N-methylpyrrolidinone |
| RP | Reversed phase |
| RT | room temperature |
| TBTU | O-benztriazol-1-yl-N,N,N',N'-tetramethyluronium tetrafluoroborate |
| tert | tertiary |
| THF | tetrahydrofuran |
| t$_{Ret}$ | retention time |

4. HPLC Analysis

HPLC: Agilent 1100 Series

MS: 1100 Series LC/MSD (API-ES+/−3000V, Quadrupol, G1946D)

MSD Signal Settings: Scan pos 120-900, Scan neg 120-900

Column: Phenomenex; Part No. 00M-4439-BO-CE; Gemini 3μ C18 110 Å; 20×2.0 mm column Eluant:
  A: 5 mM NH$_4$HCO$_3$/20 mM NH$_3$ (pH=9.5)
  B: acetonitrile HPLC grade Detection:
  SignaL: UV 254 nm (bandwide 1, reference off)
  Spectrum: range: 250-400 nm; step: 1 nm
  Peak width <0.01 min (0.1 s)

Injection: 10 μLt standard injection

Method: LCMSBAS1

| | | |
|---|---|---|
| flow: | 1.0 mL/min | |
| column temp.: | 40° C. | |
| pump gradient: | 0.0-2.5 min | 5%->95% solvent B |
| | 2.5-2.8 min | 95% solvent B |
| | 2.8-3.1 min | 95%->5% solvent B |

Compounds that elute with the injection peak are given the retention time $t_{Ret.} = 0.0$ min.

The Examples describe the biological activity of the compounds according to the invention without restricting the invention to these Examples.

Example Aurora-B Kinase Assay

A radioactive enzyme inhibition assay was developed using E. coli-expressed recombinant Xenopus laevis Aurora B wild-type protein equipped at the N-terminal position with a GST tag (amino acids 60-361) in a complex with Xenopus laevis INCENP (amino acids 790-847), which is obtained from bacteria and purified. In equivalent manner a Xenopus laevis Aurora B mutant (G96V) in a complex with Xenopus laevis INCENP$^{790-847}$ may also be used.

Expression and Purification

The coding sequence for Aurora-B$^{60-361}$ from Xenopus laevis is cloned into a modified version of pGEX-6T (Amersham Biotech) via BamHI and SalI cutting sites. The vector contains two cloning cassettes which are separated by a ribosomal binding site, allowing bi-cistronic expression. In this configuration Xenopus laevis Aurora B is expressed by the first cassette, and the Xenopus laevis INCENP$^{790-847}$ is expressed by the second cassette. The resulting vector is pAUB-IN$^{847}$.

First of all the E. coli strain BL21 (DE3) is co-transformed with pUBS520 helper plasmid and pAUB-IN$^{847}$, after which protein expression is induced using 0.3 mM IPTG at an $OD_{600}$ of 0.45-0.7. The expression is then continued for approx. 12-16 h at 23-25° C. with agitation.

The bacteria are then removed by centrifuging and the pellet is lysed in lysis buffer (50 mM Tris/Cl pH 7.6, 300 mM NaCl, 1 mM DTT, 1 mM EDTA, 5% glycerol, Roche Complete Protease Inhibitor tablets) using ultrasound, using 20-30 mL lysis buffer per liter of E. coli culture. The lysed material is freed from debris by centrifugation (12000 rpm, 45-60 min, JA20 rotor). The supernatant is incubated with 300 µL of equilibrated GST Sepharose Fast Flow (Amersham Biosciences) per liter of E. coli culture for 4-5 h at 4° C. Then the column material is washed with 30 volumes of lysis buffer and then equilibrated with 30 volumes of cleavage buffer (50 mM Tris/Cl pH 7.6, 150 mM NaCl, 1 mM DTT, 1 mM EDTA). To cleave the GST tag from Aurora B, 10 units of Prescission Protease (Amersham Biosciences) are used per milligram of substrate and the mixture is incubated for 16 h at 4° C. The supernatant which contains the cleavage product is loaded onto a 6 mL Resource Q column (Amersham Biosciences) equilibrated with ion exchange buffer (50 mM Tris/Cl pH 7.6, 150 mM NaCl, 1 mM DTT, 1 mM EDTA). The Aurora B/INCENP complex is caught as it flows through, then concentrated and loaded onto a Superdex 200 size exclusion chromatography (SEC) column equilibrated with SEC buffer (10 mM Tris/Cl pH 7.6, 150 mM NaCl, 1 mM DTT, 1 mM EDTA). Fractions which contain the AuroraB/INCENP complex are collected and concentrated using Vivaspin concentrators (molecular weight exclusion 3000-5000 Da) to a final concentration of 12 mg/mL. Aliquots (e.g. 240 ng/µL) for kinase assays are transferred from this stock solution into freezing buffer (50 mM Tris/Cl pH 8.0, 150 mM NaCl, 0.1 mM EDTA, 0.03% Brij-35, 10% glycerol, 1 mM DTT) and stored at −80° C.

Kinase Assay

Test substances are placed in a polypropylene dish (96 wells, Greiner #655 201), in order to cover a concentration frame of 10 µM-0.0001 µM. The final concentration of DMSO in the assay is 5%. 30 µL of protein mix (50 mM tris/Cl pH 7.5, 25 mM $MgCl_2$, 25 mM NaCl, 167 µM ATP, 10 ng Xenopus laevis Aurora B/INCENP complex in freezing buffer) are pipetted into the 10 µl of test substance provided in 25% DMSO and this is incubated for 15 min at RT. Then 10 µL of peptide mix (100 mM tris/Cl pH 7.5, 50 mM $MgCl_2$, 50 mM NaCl, 5 µM NaF, 5 µM DTT, 1 µCi gamma-P33-ATP [Amersham], 50 µM substrate peptide [biotin-EPLER-RLSLVPDS or multimers thereof, or biotin-EPLER-RLSLVPKM or multimers thereof, or biotin-LRRSLGL-RRSLGLRRSLGLRRSLG]) are added. The reaction is incubated for 75 min (ambient temperature) and stopped by the addition of 180 µL of 6.4% trichloroacetic acid and incubated for 20 min on ice. A multiscreen filtration plate (Millipore, MAIP NOB10) is equilibrated first of all with 100 µL 70% ethanol and then with 180 µL trichloroacetic acid and the liquids are eliminated using a suitable suction apparatus. Then the stopped kinase reaction is applied. After 5 washing steps with 180 µL 1% trichloroacetic acid in each case the lower half of the dish is dried (10-20 min at 55° C.) and 25 µL scintillation cocktail (Microscint, Packard #6013611) is added. Incorporated gamma-phosphate is quantified using a Wallac 1450 Microbeta Liquid Scintillation Counter. Samples without test substance or without substrate peptide are used as controls. The inhibitory effect of the test substance at a defined concentration of 1 µM is given as a percentage (%) of the positive control (i.e. maximum value without test substance).

The anti-proliferative activity of the compounds according to the invention is determined in the proliferation test on cultivated human tumour cells and/or in a cell cycle analysis, for example on NCI-H460 tumour cells. In both test methods compounds 1-177 exhibit good to very good activity, i.e. for example an EC50 value in the NCI-H460 proliferation test of less than 5 µmol/L, generally less than 1 µmol/L.

Measurement of the Inhibition of Proliferation on Cultivated Human Tumour Cells

To measure proliferation on cultivated human tumour cells, cells of lung tumour cell line NCI-H460 (obtained from American Type Culture Collection (ATCC)) are cultivated in RPMI 1640 medium (Gibco) and 10% foetal calf serum (Gibco) and harvested in the log growth phase. Then the NCI-H460 cells are placed in 96-well flat-bottomed plates (Falcon) at a density of 1000 cells per well in RPMI 1640 medium and incubated overnight in an incubator (at 37° C. and 5% $CO_2$). The active substances are added to the cells in various concentrations (dissolved in DMSO; DMSO final concentration: 0.1%). After 72 h incubation 20 µL Alamar-Blue reagent (AccuMed International) is added to each well, and the cells are incubated for a further 5-7 h. After incubation the colour change of the AlamarBlue reagent is determined in a Wallac Microbeta fluorescence spectrophotometer. $EC_{50}$ values are calculated using Standard Levenburg Marquard algorithms (GraphPadPrizm).

Cell cycle analyses are carried out for example using FACS analyses (Fluorescence Activated Cell Sorter) or by Cellomics Array Scan (CellCycle Analysis).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, 1.75×10⁶ NCI-H460 cells are seeded onto a 75 cm² cell culture flask, and after 24 h either 0.1% DMSO is added as control or the substance is added in various concentrations (in 0.1% DMSO). The cells are incubated for 42 h with the substance or with DMSO. Then the cells are detached with trypsin and centrifuged. The cell pellet is washed with buffered saline solution (PBS) and the cells are then fixed with 80% ethanol at −20° C. for at least 2 h. After another washing step with PBS the cells are permeabilised with Triton X-100 (Sigma; 0.25% in PBS) on ice for 5 min, and then incubated with a solution of PI (Sigma; 10 µg/mL) and RNAse (Serva; 1 mg/mL) in the ratio 9:1 for at least 20 min in the dark.

The DNA measurement is carried out in a Becton Dickinson FACS Analyzer, with an argon laser (500 mW, emission 488 nm); data are obtained and evaluated using the DNA Cell Quest Programme (BD).

Cellomics Array Scan

NCI-H460 cells are seeded into 96-well flat-bottomed dishes (Falcon) in RPMI 1640 medium (Gibco) with 10% foetal calf serum (Gibco) in a density of 2000 cells per well and incubated overnight in an incubator (at 37° C. and 5% CO₂). The active substances are added to the cells in various concentrations (dissolved in DMSO; DMSO final concentration: 0.1%). After 42 h incubation the medium is suction filtered, the cells are fixed for 10 min with 4% formaldehyde solution and Triton X-100 (1:200 in PBS) at ambient temperature and simultaneously permeabilised, and then washed twice with a 0.3% BSA solution (Calbiochem). Then the DNA is stained by the addition of 50 µL/well of 4',6-diamidino-2-phenylindole (DAPI; Molecular Probes) in a final concentration of 300 nM for 1 h at ambient temperature, in the dark. The preparations are then carefully washed twice with PBS, the plates are stuck down with black adhesive film and analysed in the Cellomics ArrayScan using the CellCycle BioApplication programme and visualised and evaluated using Spotfire.

As demonstrated by DNA staining followed by FACS or Cellomics Array Scan analysis, the inhibition of proliferation brought about by the compounds according to the invention is mediated above all by errors in chromosome segregation. Because of the accumulation of faulty segregations, massive polyploidia occurs which may finally lead to inhibition of proliferation or even apoptosis. On the basis of their biological properties the compounds of general formula (I) according to the invention, their isomers and the physiologically acceptable salts thereof are suitable for treating diseases characterised by excessive or abnormal cell proliferation.

The substances of the present invention are Aurora kinase inhibitors. On the basis of their biological properties the compounds of general formula (1) according to the invention, their isomers and the physiologically acceptable salts thereof are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. Endometrial hyperplasia)); bone diseases and cardiovascular diseases (e.g. restenosis and hypertrophy).

For example, the following cancer diseases can be treated with compounds according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas, brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodkgin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulo sarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma; vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortinsone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, imatinib, lapatinib and trastuzumab); antimetabolites (e.g. Bntifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. Estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions, —particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. In amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (1),

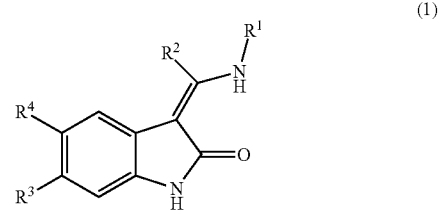

wherein $R^1$ denotes hydrogen or a group, optionally substituted by one or more identical or different $R^5$, selected from among $C_{3-10}$cycloalkyl, 3-8 membered heterocycloalkyl, $C_{6-15}$aryl and 5-15 membered heteroaryl; and $R^2$ denotes a group, optionally substituted by one or more identical or different $R^5$, selected from among $C_{6-15}$aryl and 5-15 membered heteroaryl; and $R^3$ denotes a group, optionally substituted by one or more identical or different $R^5$, selected from among $C_{2-6}$alkenyl and $C_{2-6}$alkynyl, or furan, pyrazole, pyridine, pyrimidine and pyrazine, and $R^4$ is hydrogen, $C_{1-6}$alkyl or $R^b$, and $R^5$ each independently of one another denote a group selected from among unsubstituted $R^a$, $R^b$ and $R^a$ substituted by one or more identical or different $R^b$ and/or $R^c$; and each $R^a$ is selected independently from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^b$ is a suitable group and each is independently selected from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —[N(R^g)C(O)]_2OR^e, —N(R^g)C(NR^g)OR^e, —N(R^g)C(NOH)R^e, —N(R^g)C(NR^g)SR^e and —N(R^g)C(NR^g)NR^eR^e, each R^c independently of one another denotes hydrogen or a group optionally substituted by one or more identical or different R^d and/or R^e selected from among C_{1-6}alkyl, C_{2-6}alkenyl, C_{2-6}alkynyl, C_{3-10}cycloalkyl, C_{4-11}cycloalkylalkyl, C_{6-10}aryl, C_{7-16}arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R^d is a suitable group and each is independently selected from among =O, —OR^e, C_{1-3}haloalkyloxy, —OCF_3, =S, —SR^e, =NR^e, =NOR^e, =NNR^eR^e, =NN(R^g)C(O)NR^eR^e, —NR^eR^e, —ONR^eR^e, —N(R^g)NR^eR^e, halogen, —CF_3, —CN, —NC, —OCN, —SCN, —NO, —NO_2, =N_2, —N_3, —S(O)R^e, —S(O)OR^e, —S(O)_2R^e, —S(O)_2OR^e, —S(O)NR^eR^e, —S(O)_2NR^eR^e, —OS(O)R^e, —OS(O)_2R^e, —OS(O)_2OR^e, —OS(O)NR^eR^e, —OS(O)_2NR^eR^e, —C(O)R^e, —C(O)OR^e, —C(O)SR^e, —C(O)NR^eR^e, —C(O)N(R^g)NR^eR^e, —C(O)N(R^g)OR^e, —C(NR^g)NR^eR^e, —C(NOH)R^e, —C(NOH)NR^eR^e, —OC(O)R^e, —OC(O)OR^e, —OC(O)SR^e, —OC(O)NR^eR^e, —OC(NR^g)NR^eR^e, —SC(O)R^e, —SC(O)OR^e, —SC(O)NR^eR^e, —SC(NR^g)NR^eR^e, —N(R^g)C(O)R^e, —N[C(O)R^e]_2, —N(OR^g)C(O)R^e, —N(R^g)C(NR^g)R^e, —N(R^g)N(R^g)C(O)R^e, —N[C(O)R^e]NR^eR^e, —N(R^g)C(S)R^e, —N(R^g)S(O)R^e, —N(R^g)S(O)OR^e, —N(R^g)S(O)_2R^e, —N[S(O)_2R^e]_2, —N(R^g)S(O)_2OR^e, —N(R^g)S(O)_2NR^eR^e, —N(R^g)[S(O)_2]_2R^e, —N(R^g)C(O)OR^e, —N(R^g)C(O)SR^e, —N(R^g)C(O)NR^eR^e, —N(R^g)C(O)NR^gNR^eR^e, —N(R^g)N(R^g)C(O)NR^eR^e, —N(R^g)C(S)NR^eR^e, —[N(R^g)C(O)]_2R^e, —N(R^g)[C(O)]_2R^e, —N{[C(O)]_2R^e}_2, —N(R^g)[C(O)]_2OR^e, —N(R^g)[C(O)]_2NR^eR^e, —N{[C(O)]_2OR^e}_2, —N{[C(O)]_2NR^eR^e}_2, —[N(R^g)C(O)]_2OR^e, —N(R^g)C(NR^g)OR^e, —N(R^g)C(NOH)R^e, —N(R^g)C(NR^g)SR^e and —N(R^g)C(NR^g)NR^eR^e, each R^e independently of one another denotes hydrogen or a group optionally substituted by one or more identical or different R^f and/or R^g selected from among C_{1-6}alkyl, C_{2-6}alkenyl, C_{2-6}alkynyl, C_{3-8}cycloalkyl, C_{4-11}cycloalkylalkyl, C_{6-10}aryl, C_{7-16}arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R^f is a suitable group and each is independently selected from among halogen, —CF_3 and —NR^gR^g; and each R^g independently of one another denotes hydrogen, C_{1-6}alkyl, C_{2-6}alkenyl, C_{2-6}alkynyl, C_{3-8}cycloalkyl, C_{6-10}aryl, C_{7-16}arylalkyl, 2-6 membered heteroalkyl, 3-8 membered heterocycloalkyl, 4-14 membered heterocycloalkyl, 5-12 membered heteroaryl or 6-18 membered heteroarylalkyl, optionally in the form of a prodrug, a tautomer, an enantiomer, a diastereomer or any mixture thereof, and optionally a pharmacologically acceptable acid addition salt thereof.

2. The compound according to claim 1, wherein R^3 is selected from among furan, pyrazole, pyridine, pyrimidine and pyrazine.

3. The compound according to claim 1, wherein R^4 is hydrogen.

4. The compound according to claim 1, wherein R^3 is C_{2-6}alkenyl or C_{2-6}alkynyl.

5. The compound according to claim 4, wherein R^3 is C_{2-6}alkynyl.

6. The compound according to claim 1, wherein R^2 is phenyl.

7. The compound according to claim 6, wherein R^2 denotes unsubstituted phenyl.

8. A pharmaceutical preparation, comprising as active substance one or more compounds of formula (1) according to claim 1 or a physiologically acceptable salt thereof, in combination with conventional excipients and/or carriers.

9. A pharmaceutical preparation comprising a compound of formula (1) according to claim 1 and at least one further cytostatic or cytotoxic active substance, different from formula (1).

10. A compound of formula

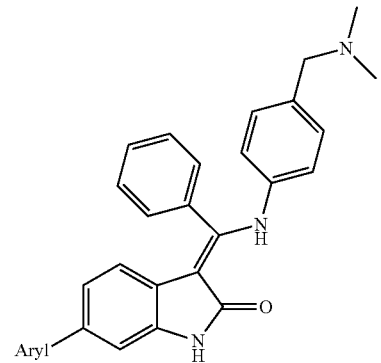

wherein Aryl is selected from the following meanings:

| No. | Aryl |
|---|---|
| 1 | ethylamino-pyrazine |
| 2 | cyclopropylmethylamino-pyrazine |
| 3 | 3-acetylphenyl |
| 5 | ethylamino-pyridine |
| 6 | dimethylamino-pyridine |

-continued
| No. | Aryl |
|---|---|
| 7 | 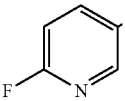 |
| 8 | 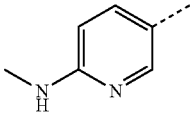 |
| 9 | 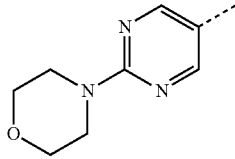 |
| 10 | 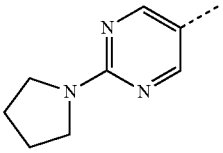 |
| 11 | 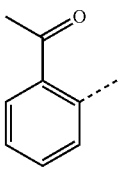 |
| 12 | 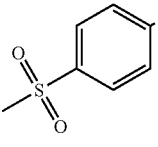 |
| 14 | 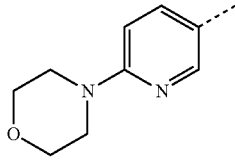 |
| 15 | 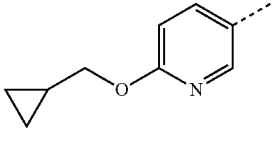 |
| 16 | 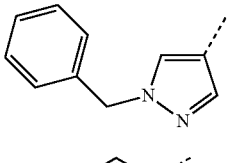 |
| 17 | 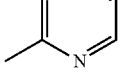 |
| 18 | 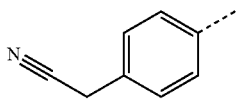 |
-continued
| No. | Aryl |
|---|---|
| 19 | 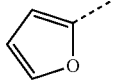 |
| 20 | 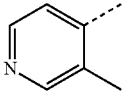 |
| 21 | 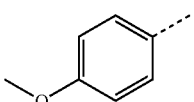 |
| 22 | 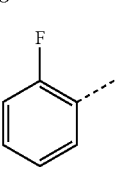 |
| 23 | 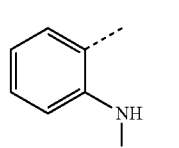 |
| 24 | 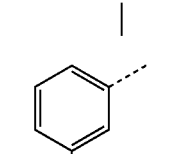 |
| 25 | 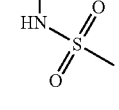 |
| 26 | 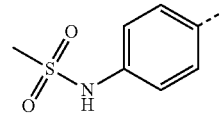 |
| 27 | 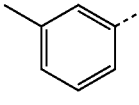 |
| 28 | 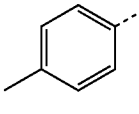 |
| 29 | 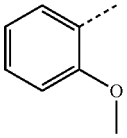 |

| No. | Aryl |
|---|---|
| 30 |  |
| 31 | 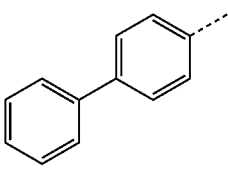 |
| 32 | 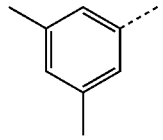 |
| 33 | 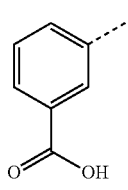 |
| 34 | 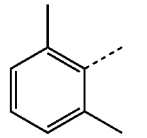 |
| 35 | 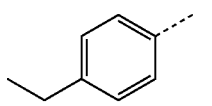 |
| 36 | 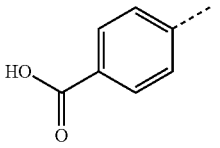 |
| 37 | 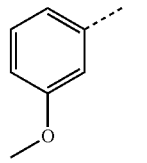 |
| 38 | 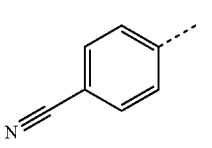 |
| 39 | 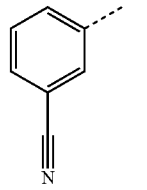 |
| 40 | 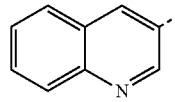 |
| 41 | 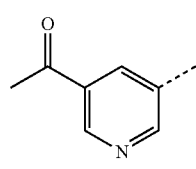 |
| 42 | 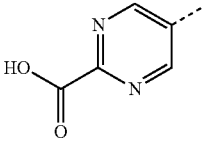 |
| 43 | 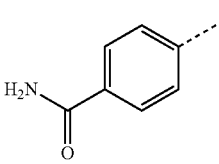 |
| 44 | 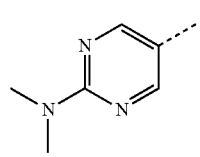 |
| 45 | 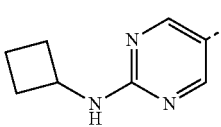 |
| 46 | 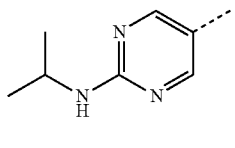 |
| 47 | 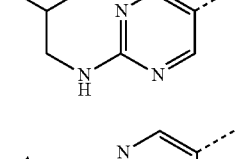 |
| 48 | 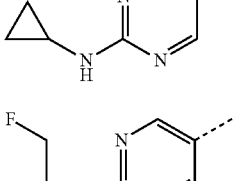 |
| 49 | 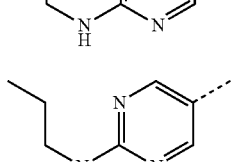 |
| 50 | 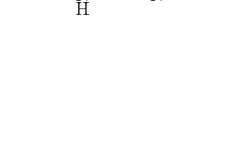 |

| No. | Aryl |
|---|---|
| 51 | 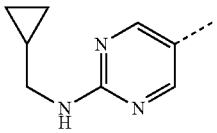 |
| 52 | 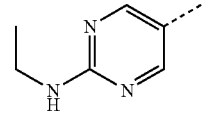 |
| 53 | 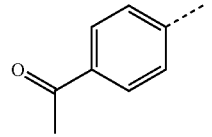 |
| 54 | 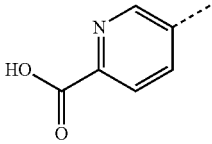 |
| 55 | 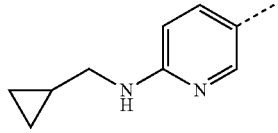 |
| 56 | 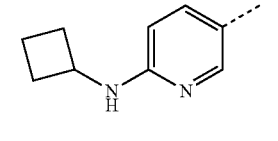 |
| 57 | 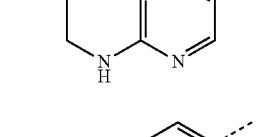 |
| 58 | 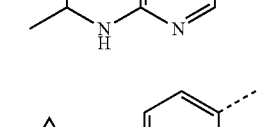 |
| 59 | 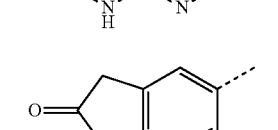 |
| 60 | 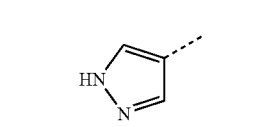 |
| 61 | 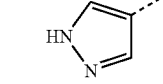 |
| No. | Aryl |
|---|---|
| 62 | 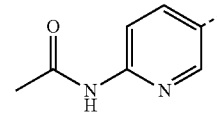 |
| 63 | 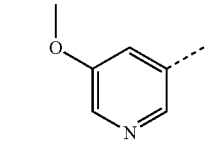 |
| 64 | 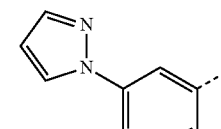 |
| 65 | 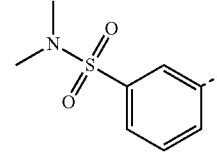 |
| 66 | 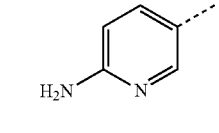 |
| 67 | 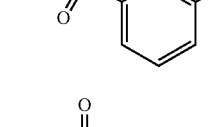 |
| 68 | 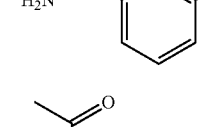 |
| 69 | 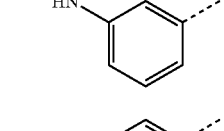 |
| 70 | 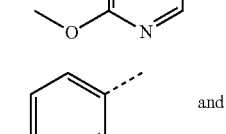 |
| 71 | 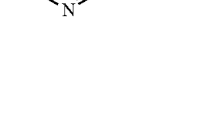 and |

| No. | Aryl |
|---|---|
| 72 | 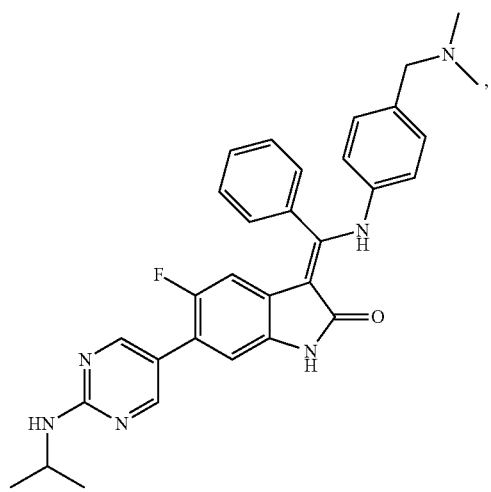 [SMILES: CC(C)Nc1ncc(-c2cc3c(cc2F)/C(=C(/Nc2ccc(CN(C)C)cc2)c2ccccc2)C(=O)N3)cn1] |
or
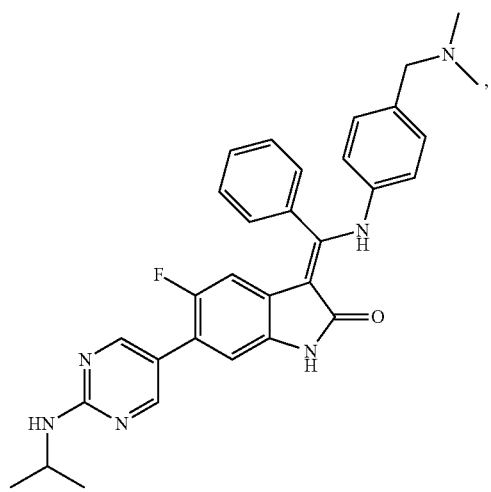 [SMILES: CC(C)Nc1ncc(-c2cc3c(cc2F)/C(=C(/Nc2ccc(CN(C)C)cc2)c2ccccc2)C(=O)N3)cn1]
and a pharmaceutically acceptable acid addition salt of any of the foregoing compounds and mixtures thereof.
11. A compound of formula:
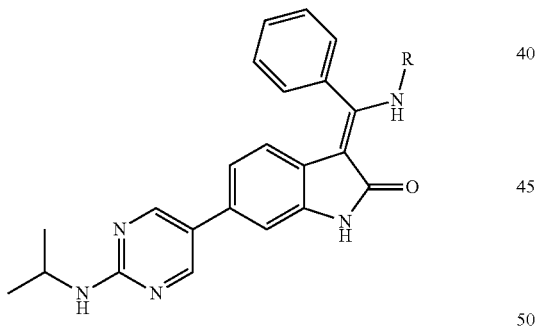
wherein R is selected from the following meanings:
| No. | R |
|---|---|
| 74 | |
| 75 | |
| 76 | |
| 77 | |
| 78 | |
| 79 | |
| 80 | |
| 81 | |
| 82 | |
| 83 | |
| 84 | |
| 85 | |

-continued

| No. | R |
|---|---|
| 86 | (5-(4-methylpiperazin-1-yl)pyridin-2-yl) |
| 87 | (2-methylpyridin-4-yl) |
| 88 | (4-(2-(pyrrolidin-1-yl)ethoxy)phenyl) |
| 89 | (4-(3-(dimethylamino)propoxy)phenyl) |
| 90 | (4-(piperidin-1-ylmethyl)phenyl) |
| 91 | (3-(pyrrolidin-1-ylmethyl)phenyl) |
| 92 | (4-(4-methylpiperazin-1-yl)phenyl) |
| 93 | (4-(3,4-dimethylpiperazin-1-yl)phenyl) and |
| 94 | (2-methylisoindolin-5-yl) | and a pharmaceutically acceptable acid addition salt of any of the foregoing compounds and mixtures thereof.

12. A compound of formula:

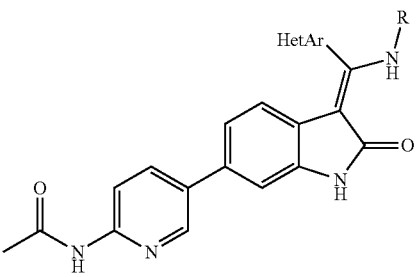

wherein HetAr and Ar are selected from the following entries:

| No. | HetAr | Aryl |
|---|---|---|
| 95 | furan-2-yl | 4-((dimethylamino)methyl)phenyl |
| 96 | 3-methylfuran-2-yl | 4-((dimethylamino)methyl)phenyl |
| 97 | pyridin-2-yl | 4-(pyrrolidin-1-ylmethyl)phenyl and |
| 98 | pyridin-4-yl | 4-((dimethylamino)methyl)phenyl | and a pharmaceutically acceptable acid addition salt of any of the foregoing compounds and mixtures thereof.

13. A compound of formula:

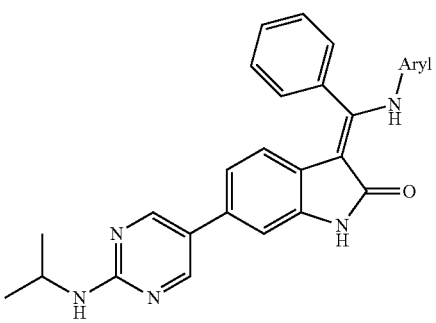

wherein Aryl is selected from the following meanings:
| No. | Aryl |
|---|---|
| 99 | 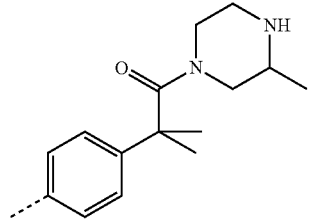 |
| 100 | 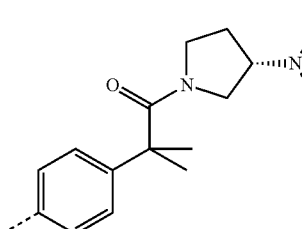 |
| 101 | 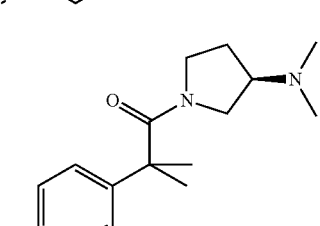 |
| 102 | 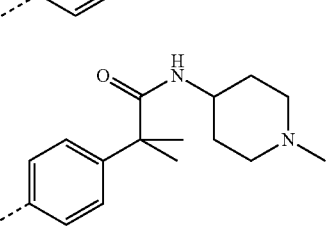 |
| 103 | 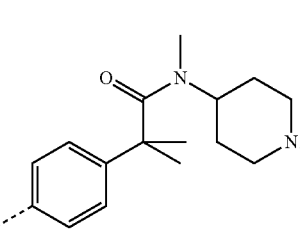 |
| 104 | 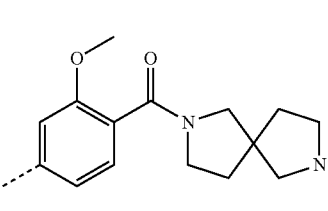 |
| 105 | 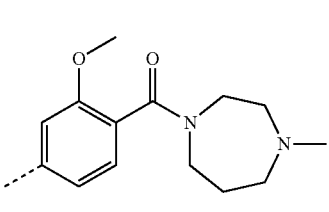 |
-continued
| No. | Aryl |
|---|---|
| 106 | 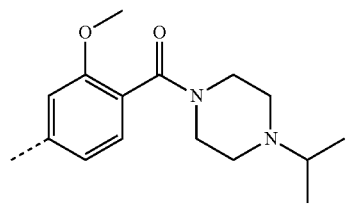 |
| 107 | 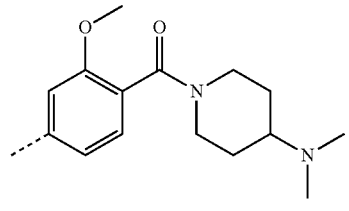 |
| 108 | 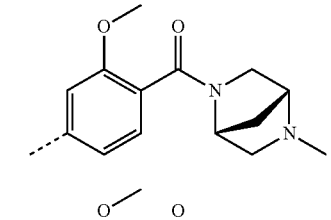 |
| 109 | 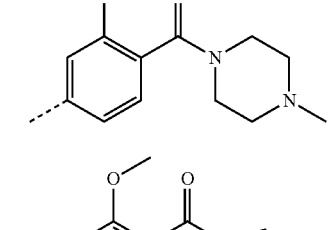 |
| 110 | 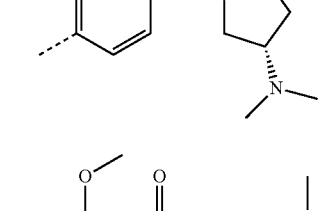 |
| 111 | 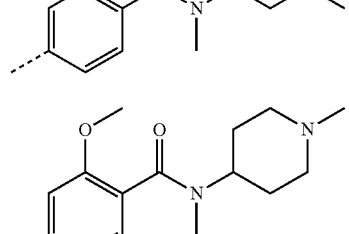 |
| 112 | 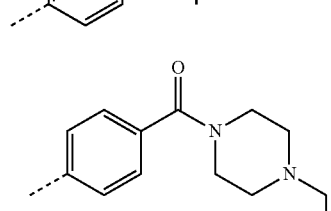 |
| 113 |  |

115
-continued
| No. | Aryl |
|---|---|
| 114 | 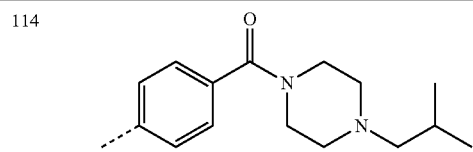 |
| 115 | 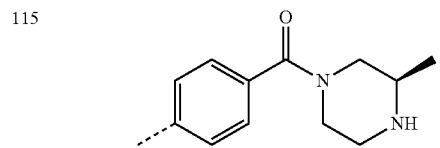 |
| 116 | 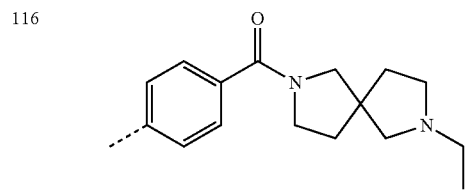 |
| 117 | 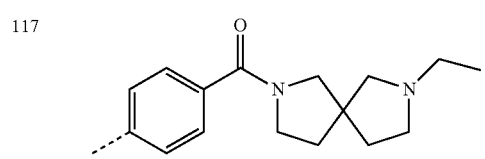 |
| 118 | 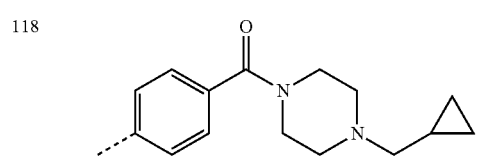 |
| 119 | 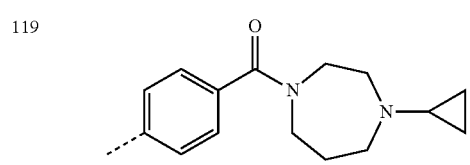 |
| 120 | 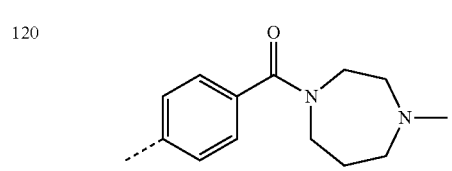 |
| 121 | 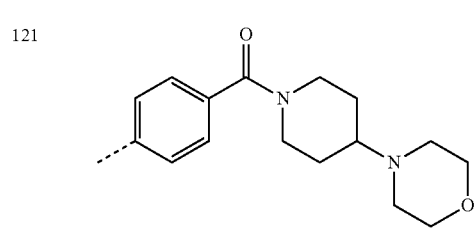 |
| 122 | 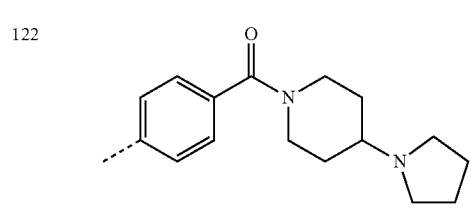 |
116
-continued
| No. | Aryl |
|---|---|
| 123 | 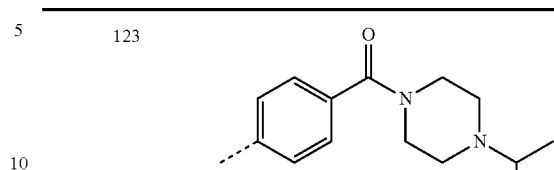 |
| 124 | 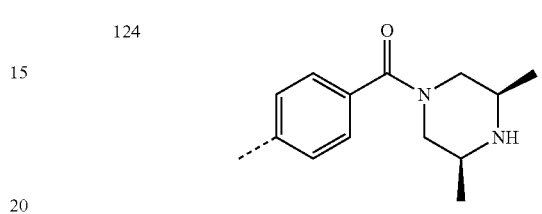 |
| 125 | 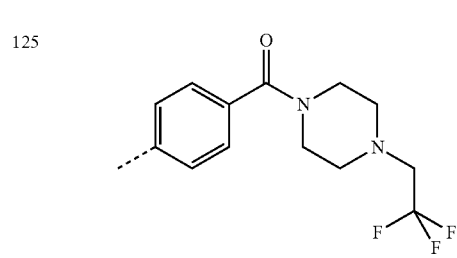 |
| 126 | 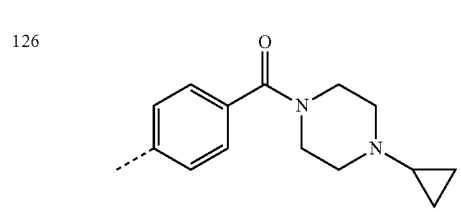 |
| 127 | 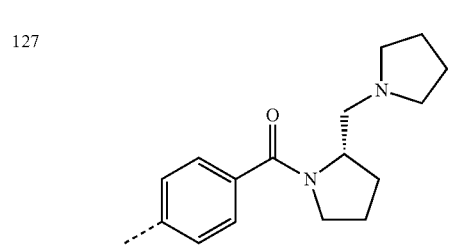 |
| 128 | 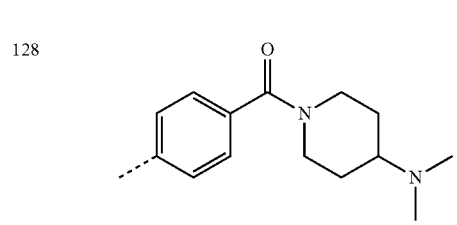 |
| 129 | 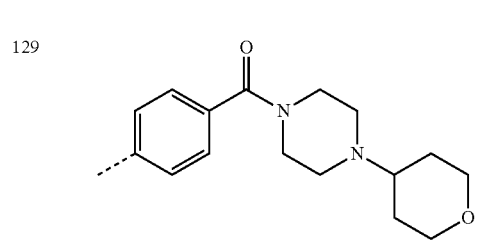 |

| No. | Aryl |
|---|---|
| 130 | 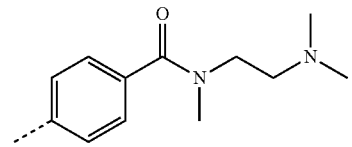 |
| 131 | 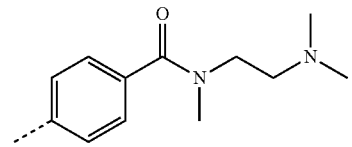 |
| 132 | 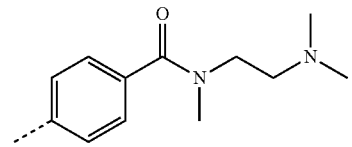 |
| 133 | 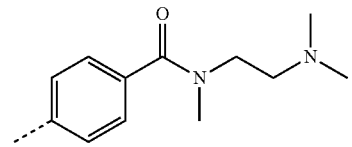 |
| 134 | 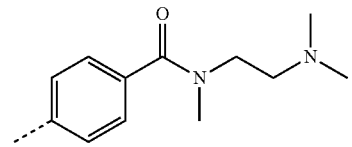 |
| 135 | 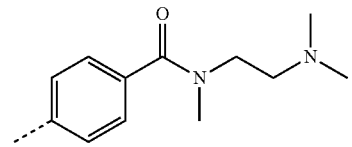 |
| 136 | 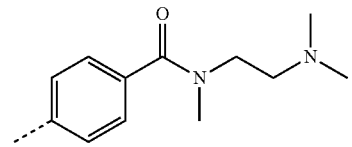 |
| 137 | 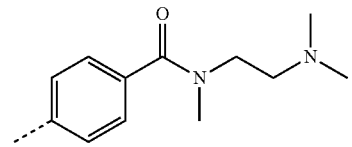 |
| No. | Aryl |
|---|---|
| 138 | 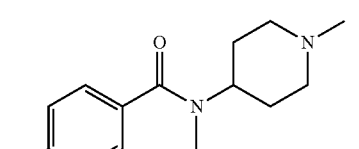 |
| 139 | 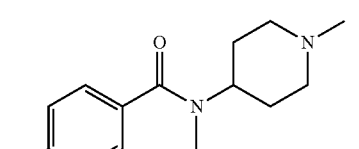 and |
| 140 | 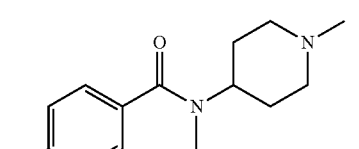 |
and a pharmaceutically acceptable acid addition salt of any of the foregoing compounds and mixtures thereof.
14. A compound of formula:
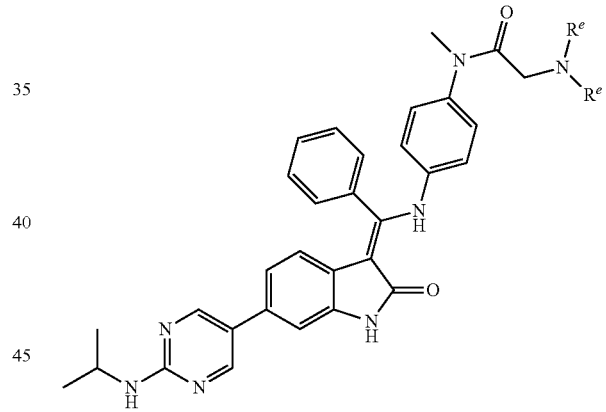
wherein $NR^e R^e$ is selected from the following meanings:
| No. | $NR^e R^e$ |
|---|---|
| 141 | 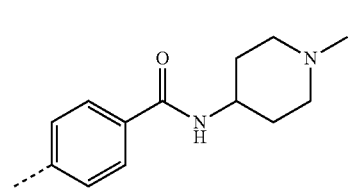 |
| 142 | 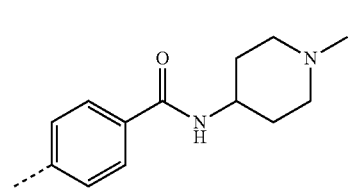 |
| 143 | 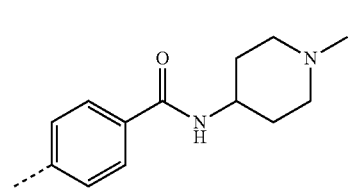 |

-continued
| No. | NReRe |
|---|---|
| 144 | 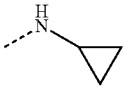 |
| 145 | 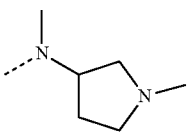 |
| 146 | 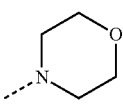 |
| 147 | 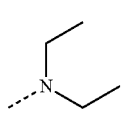 |
-continued
| No. | NReRe |
|---|---|
| 148 | 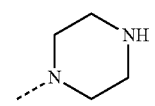 |
| 149 | 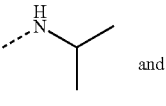 |
| 150 | 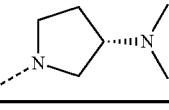 |
and a pharmaceutically acceptable acid addition salt of any of the foregoing compounds and mixtures thereof.
15. A compound selected from the group consisting of:
| No. | Compound |
|---|---|
| 151 | 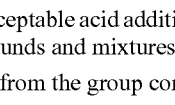 |
| 152 | 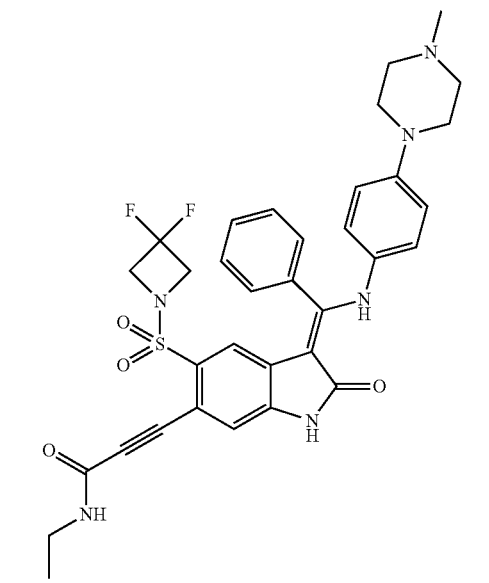 [SMILES: CCNC(=O)C#Cc1cc2c(cc1S(=O)(=O)N1CC(F)(F)C1)/C(=C(/Nc1ccc(N3CCN(C)CC3)cc1)c1ccccc1)C(=O)N2] |

| No. | Compound |
|---|---|
| 153 | 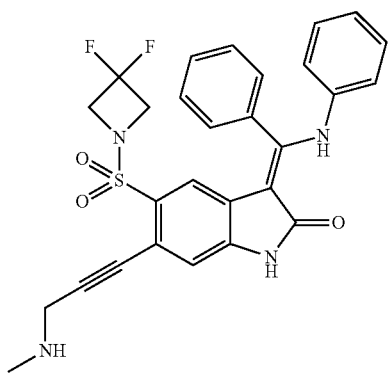 [SMILES: CNCC#Cc1cc2c(cc1S(=O)(=O)N1CC(F)(F)C1)/C(=C(/Nc1ccccc1)c1ccccc1)C(=O)N2] |
| 154 | 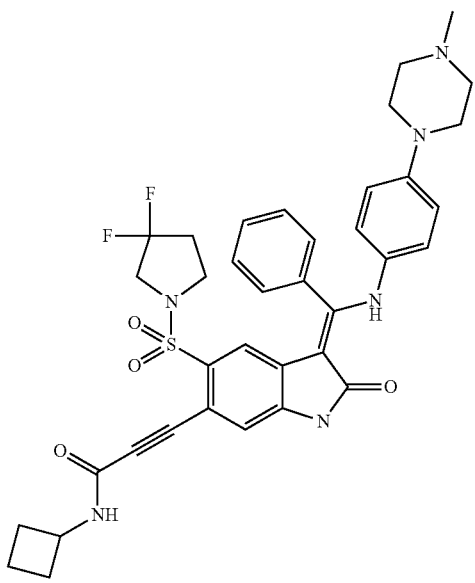 [SMILES: CN1CCN(c2ccc(N/C(=C3\C(=O)Nc4cc(C#CC(=O)NC5CCC5)c(S(=O)(=O)N5CCC(F)(F)C5)cc43)c3ccccc3)cc2)CC1] |
| 155 | 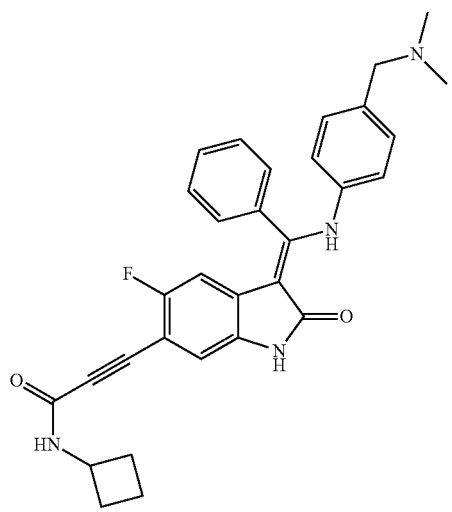 [SMILES: CN(C)Cc1ccc(N/C(=C2\C(=O)Nc3cc(C#CC(=O)NC4CCC4)c(F)cc32)c2ccccc2)cc1] |

-continued
| No. | Compound |
|---|---|
| 156 | 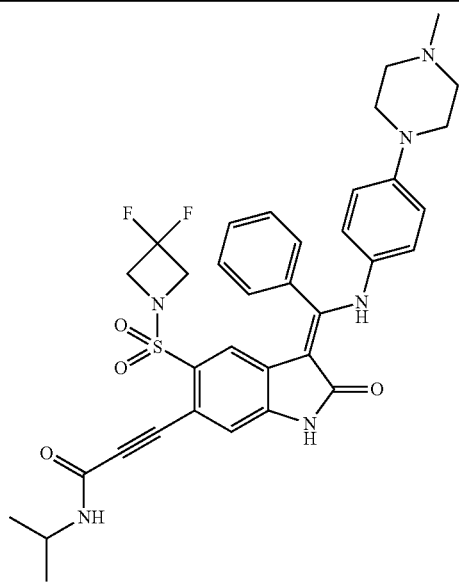 |
| 157 | 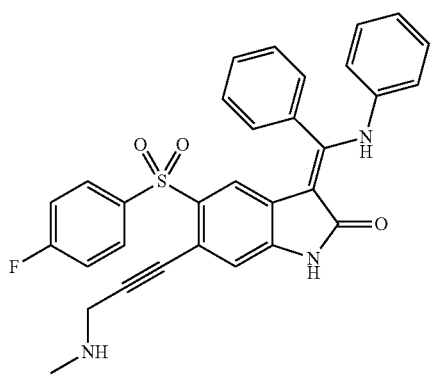 [SMILES: CNCC#Cc1cc2c(cc1S(=O)(=O)c1ccc(F)cc1)/C(=C(/Nc1ccccc1)c1ccccc1)C(=O)N2] |
| 158 | 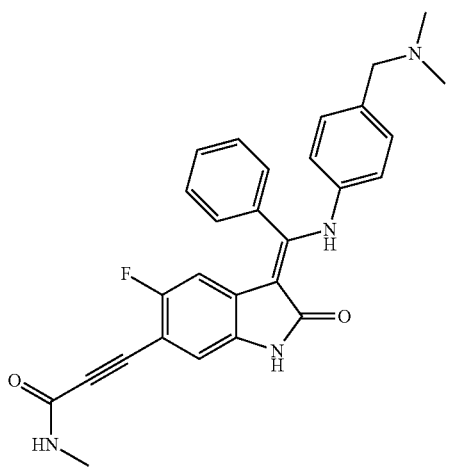 [SMILES: CNC(=O)C#Cc1cc2c(cc1F)/C(=C(/Nc1ccc(CN(C)C)cc1)c1ccccc1)C(=O)N2] |

-continued
| No. | Compound |
|---|---|
| 159 | 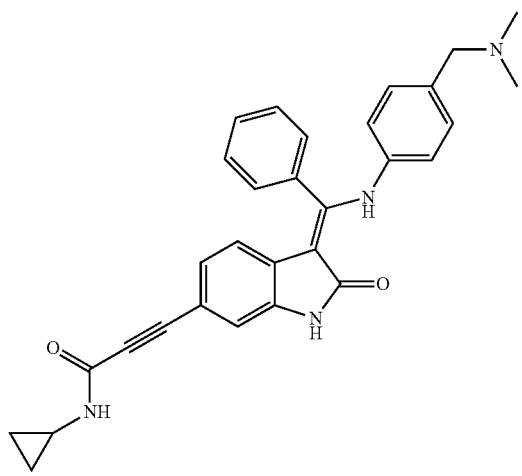 [SMILES: CN(C)Cc1ccc(N/C(=C2\C(=O)Nc3cc(C#CC(=O)NC4CC4)ccc32)c2ccccc2)cc1] |
| 160 | 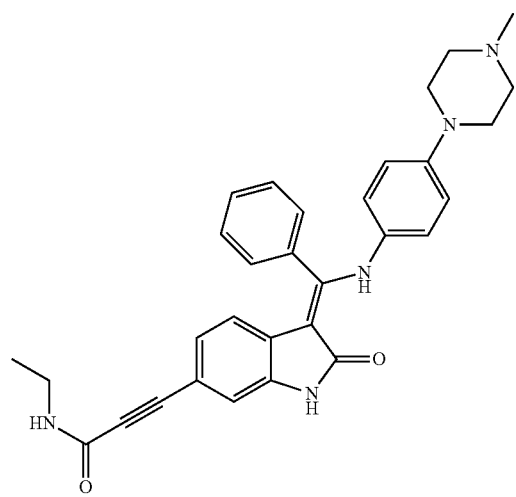 [SMILES: CCNC(=O)C#Cc1ccc2c(c1)NC(=O)/C2=C(\Nc1ccc(N2CCN(C)CC2)cc1)c1ccccc1] |
| 161 | 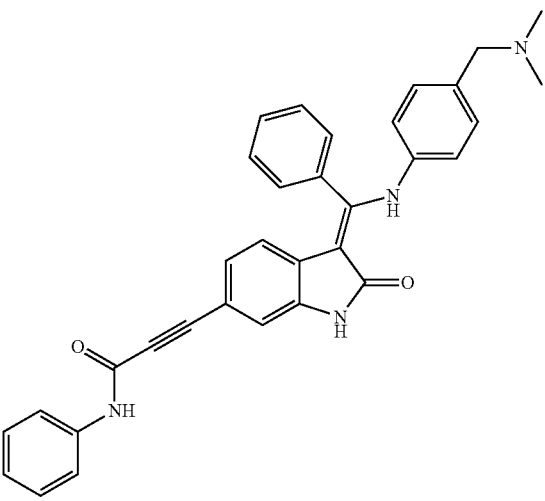 [SMILES: CN(C)Cc1ccc(N/C(=C2\C(=O)Nc3cc(C#CC(=O)Nc4ccccc4)ccc32)c2ccccc2)cc1] |

-continued
| No. | Compound |
|---|---|
| 162 | 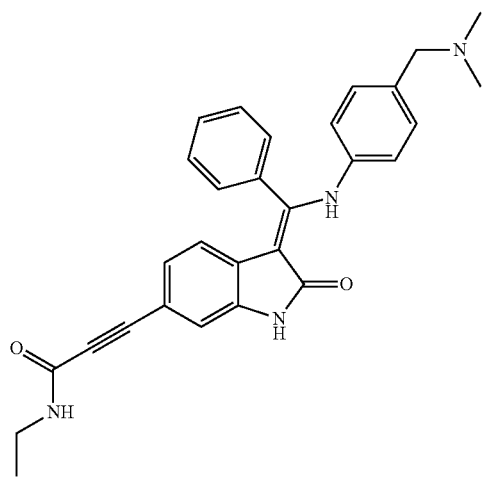 [SMILES: CCNC(=O)C#Cc1ccc2c(c1)NC(=O)/C2=C(\Nc1ccc(CN(C)C)cc1)c1ccccc1] |
| 163 | 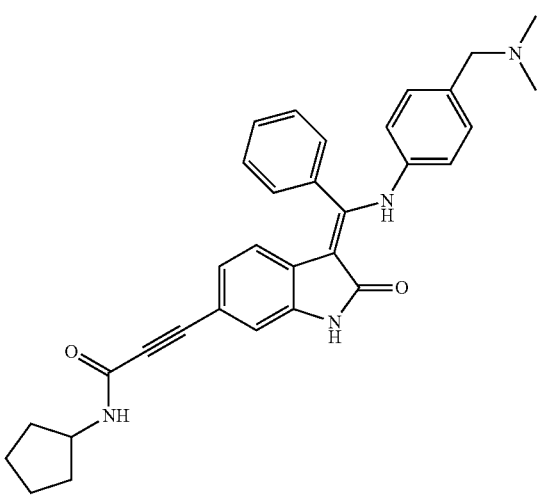 [SMILES: CN(C)Cc1ccc(N/C(=C2\C(=O)Nc3cc(C#CC(=O)NC4CCCC4)ccc32)c2ccccc2)cc1] |
| 164 | 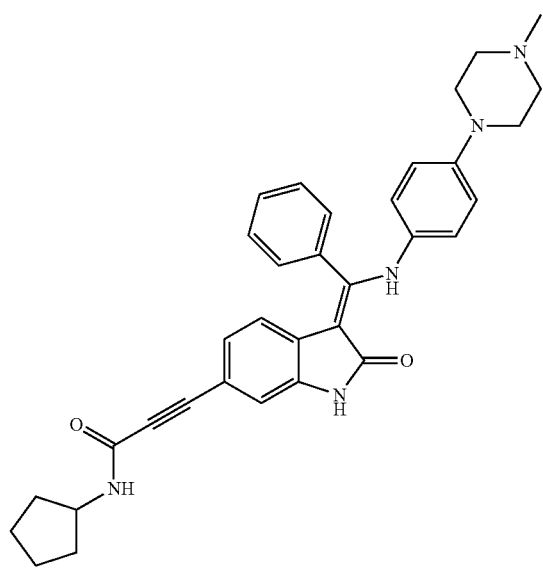 [SMILES: CN1CCN(c2ccc(N/C(=C3\C(=O)Nc4cc(C#CC(=O)NC5CCCC5)ccc43)c3ccccc3)cc2)CC1] |

-continued
| No. | Compound |
|---|---|
| 165 | 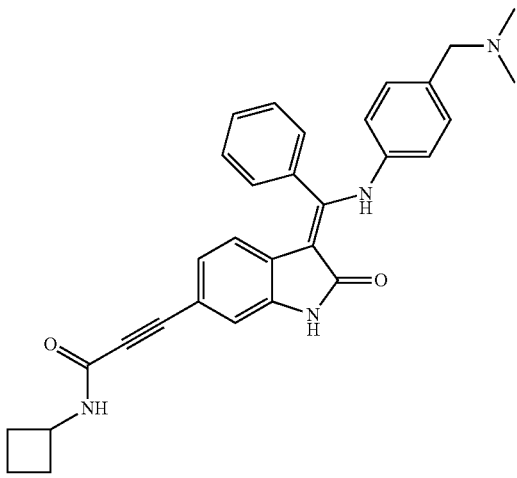 [SMILES: CN(C)Cc1ccc(N/C(=C2\C(=O)Nc3cc(C#CC(=O)NC4CCC4)ccc32)c2ccccc2)cc1] |
| 166 | 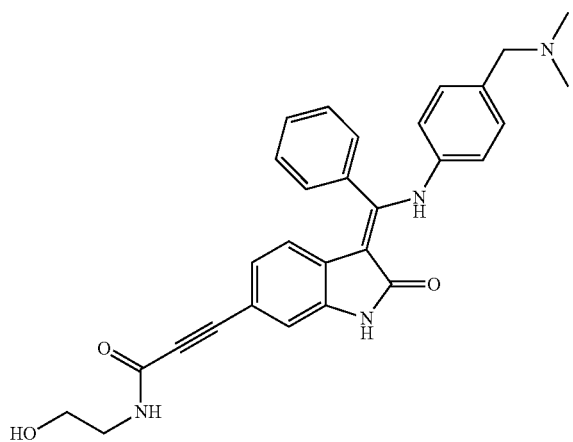 [SMILES: CN(C)Cc1ccc(N/C(=C2\C(=O)Nc3cc(C#CC(=O)NCCO)ccc32)c2ccccc2)cc1] |
| 167 | 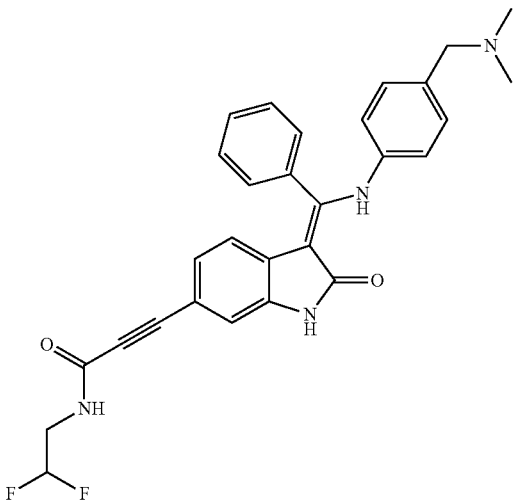 [SMILES: CN(C)Cc1ccc(N/C(=C2\C(=O)Nc3cc(C#CC(=O)NCC(F)F)ccc32)c2ccccc2)cc1] |

-continued
| No. | Compound |
|---|---|
| 168 | 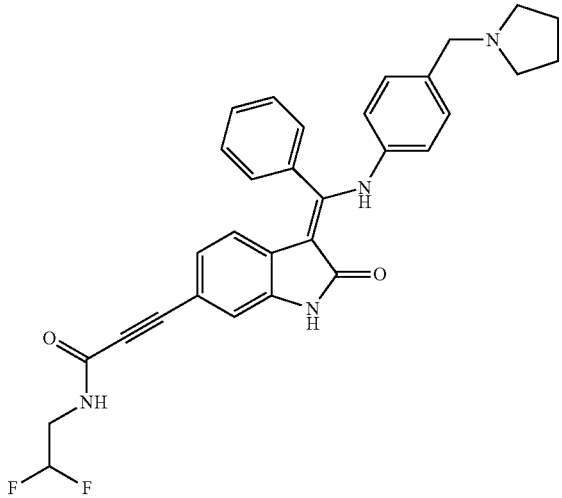 [SMILES: O=C(C#Cc1ccc2c(c1)NC(=O)/C2=C(\Nc1ccc(CN2CCCC2)cc1)c1ccccc1)NCC(F)F] |
| 169 | 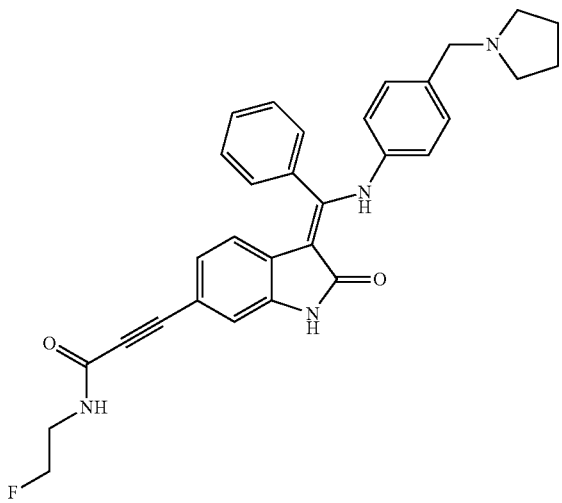 [SMILES: O=C(C#Cc1ccc2c(c1)NC(=O)/C2=C(\Nc1ccc(CN2CCCC2)cc1)c1ccccc1)NCCF] |
| 170 | 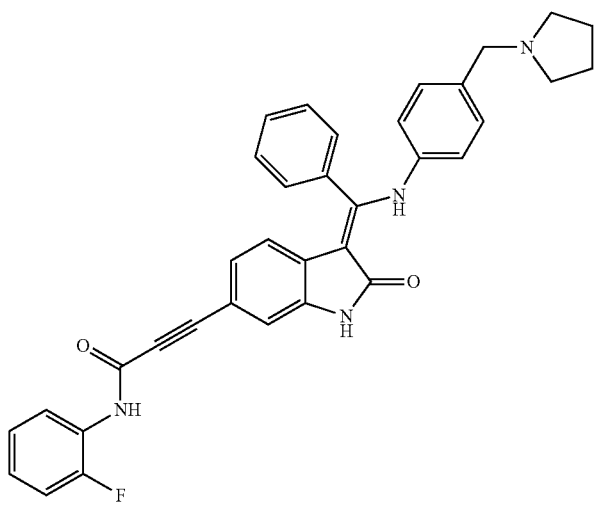 [SMILES: O=C(C#Cc1ccc2c(c1)NC(=O)/C2=C(\Nc1ccc(CN2CCCC2)cc1)c1ccccc1)Nc1ccccc1F] |

-continued
| No. | Compound |
|---|---|
| 171 | 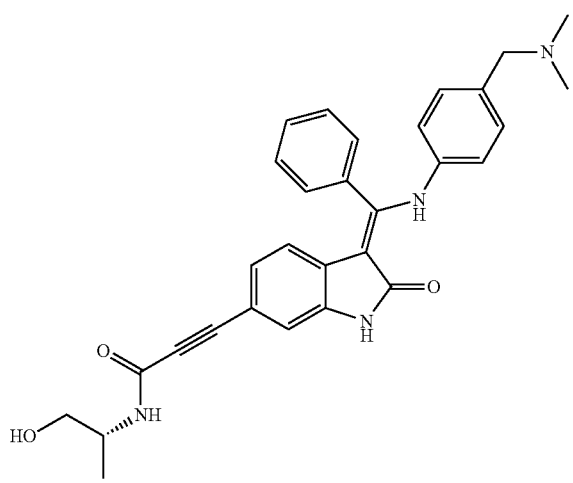 Chiral |
| 172 | 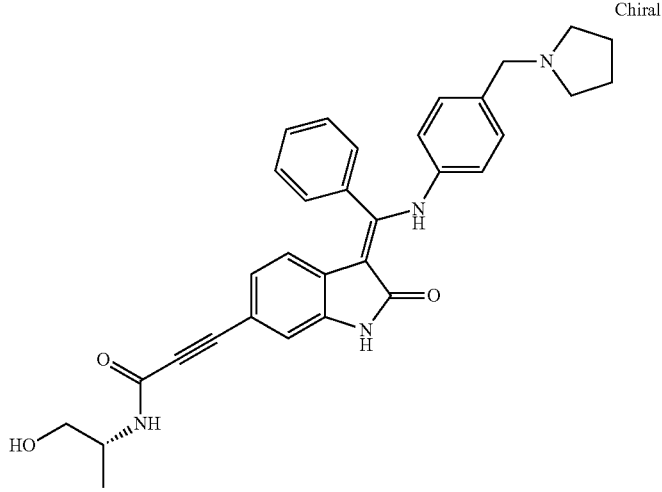 [SMILES: C[C@H](CO)NC(=O)C#Cc1ccc2c(c1)NC(=O)/C2=C(\Nc1ccc(CN2CCCC2)cc1)c1ccccc1] Chiral |
| 173 | 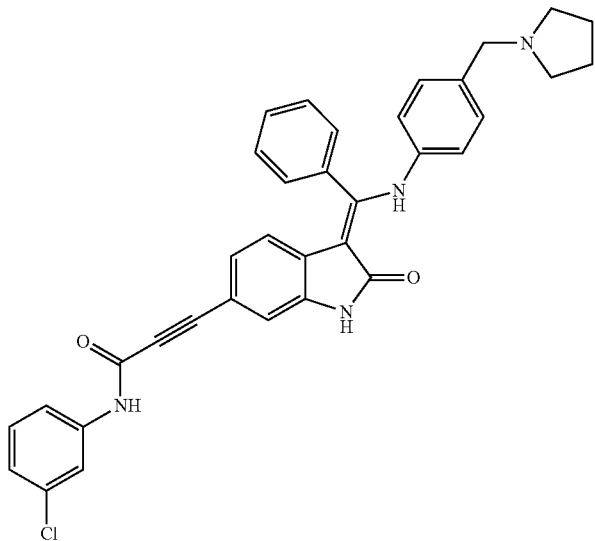 [SMILES: O=C(C#Cc1ccc2c(c1)NC(=O)/C2=C(\Nc1ccc(CN2CCCC2)cc1)c1ccccc1)Nc1cccc(Cl)c1] |

-continued
| No. | Compound |
|---|---|
| 174 | 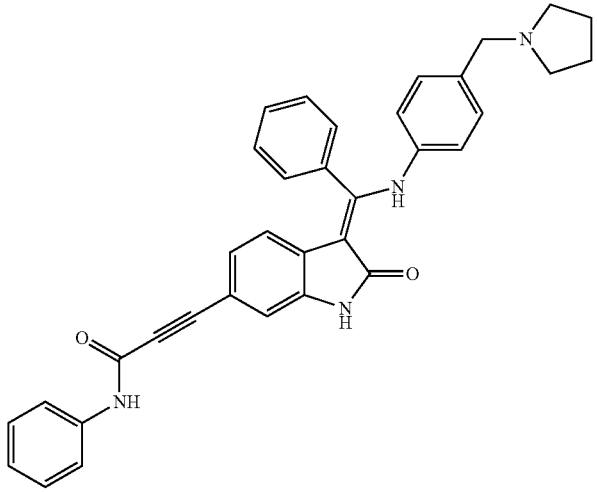 [SMILES: O=C(C#Cc1ccc2c(c1)NC(=O)/C2=C(\Nc1ccc(CN2CCCC2)cc1)c1ccccc1)Nc1ccccc1] |
| 175 | 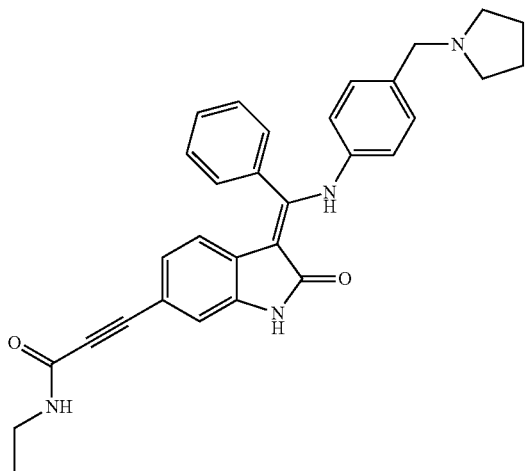 [SMILES: CCNC(=O)C#Cc1ccc2c(c1)NC(=O)/C2=C(\Nc1ccc(CN2CCCC2)cc1)c1ccccc1] |
| 176 | 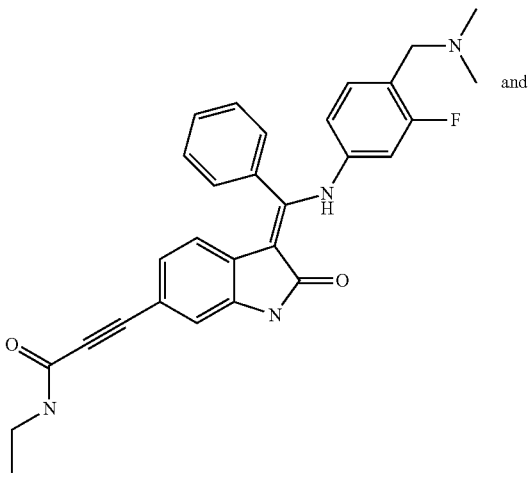 [SMILES: CCNC(=O)C#Cc1ccc2c(c1)NC(=O)/C2=C(\Nc1ccc(CN(C)C)c(F)c1)c1ccccc1] and |

| No. | Compound |
|---|---|
| 177 | 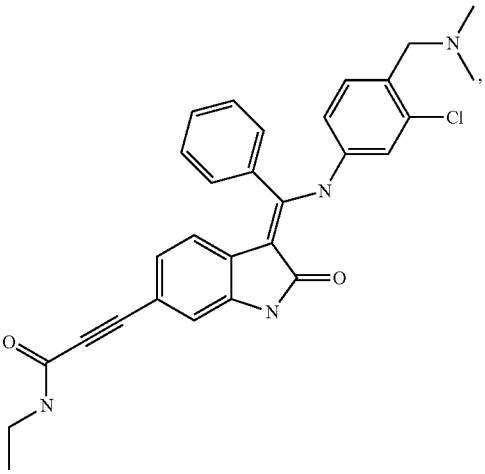 [SMILES: CCNC(=O)C#Cc1ccc2c(c1)NC(=O)/C2=C(\Nc1ccc(CN(C)C)c(Cl)c1)c1ccccc1] |
and a pharmaceutically acceptable acid addition salt of any of the foregoing compounds and mixtures thereof.
* * * * *